US006278007B1

(12) United States Patent
Inaoka et al.

(10) Patent No.: US 6,278,007 B1
(45) Date of Patent: Aug. 21, 2001

(54) (POLY)ALKYLENE GLYCOL HIGHER ALKYL ETHER DERIVATIVE COMPOSITION AND DETERGENT, LUBRICANT, AND DERMATOLOGIC MEDICINE FOR EXTERNAL USE CONTAINING THE COMPOSITION

(75) Inventors: Toru Inaoka; Kenji Rakutani; Yukio Kadono, all of Yokohama; Yoshiyuki Onda, Suita, all of (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/309,011

(22) Filed: May 10, 1999

(30) Foreign Application Priority Data

Jun. 5, 1998 (JP) ................................. 10-158086
Jun. 8, 1998 (JP) ................................. 10-159324
Jun. 15, 1998 (JP) ................................. 10-167248

(51) Int. Cl.[7] ................. C07B 35/08; C07C 51/347; C11C 3/00; A01N 37/02; A01N 37/00
(52) U.S. Cl. .................. 554/126; 514/552; 514/506; 514/847; 514/844; 514/873
(58) Field of Search .................. 554/126; 514/552, 514/506, 847, 844, 873

(56) References Cited

U.S. PATENT DOCUMENTS

| 4,171,455 | 10/1979 | Tomita et al. ............. 568/625 |
| 5,581,001 | * 12/1996 | O'Lenick .................. 554/227 |
| 5,656,664 | * 8/1997 | O'Lenick .................. 514/552 |

FOREIGN PATENT DOCUMENTS

| 0 850 907 A2 | 7/1998 | (EP) ............. C07C/43/11 |
| 53-130613 | 11/1978 | (JP) ............. C07C/43/10 |
| 9-87223 | 3/1997 | (JP) ............. C07C/43/04 |
| 10-168014 | 6/1998 | (JP) ............. C07C/43/11 |
| 10-218820 | 8/1998 | (JP) ............. C07C/43/11 |
| 10-251215 | 9/1998 | (JP) ............. C07C/305/10 |
| 96/36583 | 11/1996 | (WO) ............. C07C/43/04 |

OTHER PUBLICATIONS

Registry file from Cas for US patent 5,581,001, AN 1997:225097.), Aug. 1997.*

* cited by examiner

Primary Examiner—Johann Richter
Assistant Examiner—Diedra Faulkner
(74) Attorney, Agent, or Firm—Fish & Richardson P.C.

(57) ABSTRACT

A (poly)alkylene glycol higher alkyl ether derivative composition characterized by comprising 30–90 mol. % of (B1) (poly)alkylene glycol higher alkyl ether derivative and 70–10 mol. % of (B2) (poly)alkylene glycol higher alkyl ether derivative, respectively having a methyl group for $R^1$ and an alkyl group of not less than two carbon atoms for $R^1$ in the general formula (1) representing the derivatives:

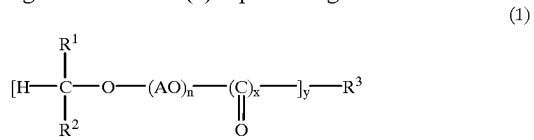

(wherein $R^1$ and $R^2$ represent alkyl groups whose total number of carbon atoms is in the range of 7–29, the number of carbon atoms of $R^2$ is larger than the number of carbon atoms of $R^1$, A represents a lower alkylene group, n represents a real number in the range of 1–300 on average, x represents 0 or 1, y represents a real number in the range of 1–10 on average, and $R^3$ represents an optionally substituted organic residue of 1–60 carbon atoms [excluding the carbon atoms of the substituent]) and a deterging agent, a lubricating agent, or a dermatological medicine for external use containing the (poly)alkylene glycol higher alkyl ether derivative composition. The composition possesses such characteristic features as containing no oil-soluble component of low molecular weight, emitting odor sparingly, exhibiting a low stimulating property, having no foaming property, abounding in penetrating force, allowing thorough separation of the foam from a deterged article, and enjoying such low viscosity as to allow great ease of handling.

4 Claims, 10 Drawing Sheets

(POLY)ALKYLENE GLYCOL HIGHER ALKYL ETHER DERIVATIVE COMPOSITION AND DETERGENT, LUBRICANT, AND DERMATOLOGIC MEDICINE FOR EXTERNAL USE CONTAINING THE COMPOSITION

TECHNICAL FIELD

This invention relates to a novel (poly)alkylene glycol higher alkyl ether derivative composition and more particularly to a (poly)alkylene glycol higher alkyl ether derivative composition useful as detergent, lubricant, dermatologic medine for external use, solvent, plasticizer, polymerizing monomer, and the like.

BACKGROUND ART

The present inventors created a higher secondary alcohol alkoxylate composition of a specific structure as a novel substance and discovered that this higher secondary alcohol alkoxylate composition possessed an excellent quality as a detergent. They formerly filed patent applications covering their inventions pertinent to the composition (patent application Ser. No. 08-327,365 and patent application Ser. No. 08-327,366).

This invention consists in providing a novel (poly) alkylene glycol higher alkyl ether derivative composition which is a derivative of the higher secondary alcohol alkoxylate composition mentioned above.

This invention further consists in providing a novel detergent, lubricant, or dermatologic medicine for external use which contains the (poly)alkylene glycol higher alkyl ether derivative composition mentioned above.

DISCLOSURE OF THE INVENTION

This invention concerns a (poly)alkylene glycol higher alkyl ether derivative composition characterized by comprising 30–90 mol. % of (B1) (poly)alkylene glycol higher alkyl ether derivative and 70–10 mol. % of (B2) (poly)alkylene glycol higher alkyl ether derivative, espectively having a methyl group for $R^1$ and an alkyl group of not less than two carbon atoms for $R^1$ in the general formula (1) representing the derivatives:

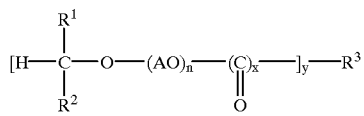
(1)

(wherein $R^1$ and $R^2$ represent alkyl groups whose total number of carbon atoms is in the range of 7–29, the number of carbon atoms of $R^2$ is larger than the number of carbon atoms of $R^1$, A represents a lower alkylene group, n represents a real number in the range of 1–300 on average, x represents 0 or 1, y represents a real number in the range of 1–10 on average, and $R^3$ represents an optionally substituted organic residue of 1–60 carbon atoms [excluding the carbon atoms of the substituent]).

This invention further concerns the (poly)alkylene glycol higher alkyl ether derivative composition mentioned above, wherein the general formula (1) mentioned above is such that A represents an alkylene group of 2–4 carbon atoms, n represents a real number in the range of 1–20 on average, x represents 0, y represents 1, $R^3$ represents $R^4COOM$, $R^4$ represents an alkylene group of 1–4 carbon atoms, and M represents a hydrogen atom, an alkali metal atom, an alkaline earth metal atom, an ammonium group, or an alkanol ammonium group.

This invention further concerns the (poly)alkylene glycol higher alkyl ether derivative composition mentioned above, wherein the general formula (1) mentioned above is such that A represents an alkylene group of 2–4 carbon atoms, X represents 0, y represents 1, and $R^3$ represents an alkyl group of 1–50 carbon atoms, a cycloalkyl group, an alkenyl group, or an aryl group.

This invention further concerns the (poly)alkylene glycol higher alkyl ether derivative composition mentioned above, wherein the general formula (1) mentioned above is such that A represents an alkylene group of 2–4 carbon atoms, x represents 1, y represents a real number in the range of 1–4 on average, $R^3$ represents $R^5[COOM]_z$, $R^5$ represents a hydrocarbon residue of 1–60 carbon atoms, M represents a hydrogen atom, an alkali metal atom, an alkaline earth metal atom, an ammonium group, or an alkanol ammonium group, z represents a real number in the range of 0–3, and y+z represents a real number in the range of 1–4.

This invention further concerns the (poly)alkylene glycol higher alkyl ether derivative composition mentioned above, wherein the general formula (1) mentioned above is such that A represents an alkylene group of 2–4 carbon atoms, x represents 1, y represents 1, and $R^3$ represents a residue resulting from the exclusion of a carboxyl group from a monohydroxymonocarboxylic acid of 10–24 carbon atoms or a residue resulting from the exclusion of a carboxyl group from a (poly)ester derived by the condensation of a monohydroxymonocarboxylic acid of 10–24 carbon atoms.

This invention further concerns a detergent, a lubricant, or a dermatologic medicine for external use containing the (poly)alkylene glycol higher alkyl ether derivative composition mentioned above.

BEST MODE OF EMBODYING THE INVENTION

Figure 1:
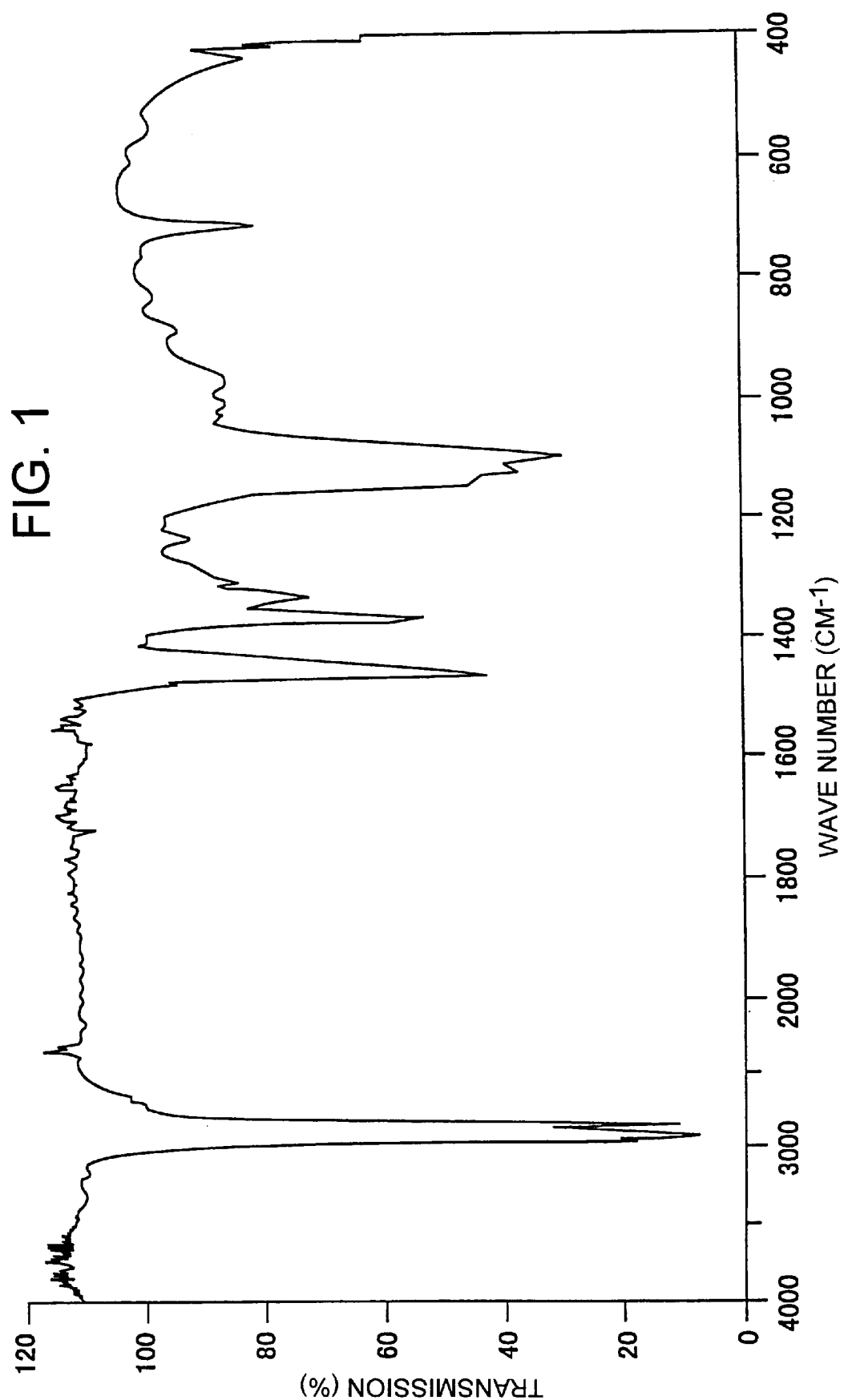
FIG. 1 is a diagram showing the infrared absorption spectrum of the compound obtained in Example 1.

The (poly)alkylene glycol higher alkyl ether derivative composition of this invention is characterized by comprising 30–90 mol. % of (B1) (poly)alkylene glycol higher alkyl ether derivative and 70–10 mol. % of (B2) (poly)alkylene glycol higher alkyl ether derivative, respectively having a methyl group for $R^1$ and an alkyl group of not less than two carbon atoms for $R^1$ in the general formula (1) representing the derivatives:

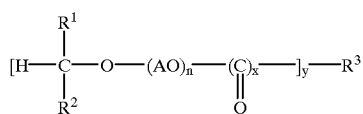

(1)

(wherein $R^1$ and $R^2$ represent alkyl groups whose total number of carbon atoms is in the range of 7–29, the number of carbon atoms of $R^2$ is larger than the number of carbon atoms of $R^1$, A represents a lower alkylene group, n represents a real number in the range of 1–300 on average, x represents 0 or 1, y represents a real number in the range of 1–10 on average, and $R^3$ represents an optionally substituted organic residue of 1–60 carbon atoms [excluding the carbon atoms of the substituent]).

In the general formula (1) mentioned above, the alkyl groups represented by $R^1$ and $R^2$ are preferred to be linear alkyl groups, the total of the carbon atoms of $R^1$ and the carbon atoms of $R^2$ is in the range of 7–29, preferably in the range of 9–19, and the number of the carbon atoms of $R^2$ is not less than the number of the carbon atoms of $R^1$ (number of carbon atoms of $R^1 \leq$ number of carbon atoms of $R^2$). If the total of the number of the carbon atoms of $R^1$ and the number of the carbon atoms of $R^2$ is not more than 6, the composition will be at a disadvantage in suffering from deficiency in such properties as lubricity and surface activity because of unduly small lengths of the alkyl groups. Conversely, if the total of the number of the carbon atoms of $R^1$ and the number of the carbon atoms of $R^2$ is not less than 30, the composition will be at a disadvantage in suffering from deficiency in lubricity, surface activity, and low-temperature flowability because of unduly large lengths of the alkyl groups. By controlling the total of the number of the carbon atoms of $R^1$ and the number of the carbon atoms of $R^2$ in the range mentioned above, therefore, the composition is enabled to manifest such characteristic properties as low-temperature flowability, lubricity, friction reducing property, compatibility, release property, and surface activity satisfactorily. The control may be justly called an advantageous condition for the sake of heightening the usefulness of the composition as a lubricant, a detergent, a dermatological medicine for external use, or other similar agents.

The composition has an essential requirement of comprising 30–90 mol. %, preferably 40–80 mol. %, of the (B1) derivative and 70–10 mol. %, preferably 60–20 mol. %, of the (B2) derivative, respectively having a methyl group for $R^1$ and an alkyl group of not less than two carbon atoms for $R^1$, in the general formula (1) mentioned above. If the proportion of the (B1) derivative exceeds 90 mol. %, the composition will be at a disadvantage in incurring a degradation in the performance thereof manifested as a lubricant, a detergent, or a dermatologic medicine for external use because of a decline in low-temperature flowability or a decline in surface activity. In contrast, if the proportion of the (B1) derivative is less than 30 mol. %, the composition will be at a disadvantage in not only inevitably admitting impurities by reason of manufacture to the extent of entailing a degradation in the performance thereof manifested as a lubricant, a detergent, or a dermatologic medicine for external use but also bringing such economic defects as increasing the cost of production because of an elongation of reaction time and a decline of productivity.

The lower alkylene group represented by A in the general formula (1) mentioned above is an alkylene group of 2–8 carbon atoms, preferably 2–4 carbon atoms. If the numbeur of carbon atoms of the alkylene group exceeds 9, the composition will be at a disadvantage as in being unable to fit a wide range of uses because of high cost of production and unduly strong hydrophobicity. As concrete examples of the oxyalkylene group which is represented by AO, therefore, oxyethylene group, oxypropylene group, oxybutylene group, oxypentylene group, oxyhexylene group, oxyheptylene group, oxyoctylene group, and oxyphenylethylene group may be cited. Among other oxyalkylene groups mentioned above, oxyethylene group, oxypropylene group, and oxybutylene group prove particularly preferable. As defined by AO in the general formula (1) mentioned above, these oxyalkylene groups may exist either singly or in the form of a combination of two or more members. When two or more oxyalkylene groups occur in combination, they may be disposed either randomly simultaneously or in a blocked state separately. They may be in a configuration such that part of the long chain of an oxyethylene group is an oxypropylene group.

The letter n in the general formula (1) mentioned above represents a real number in the range of 1–300, preferably 1–200, on average. If this real numer exceeds 300, the composition will be at a disadvantage in finding only limited utility in any field strongly in need of low-temperature flowability because the lubricity and the surface activity are insufficient, the viscosity is unduly high, the biodegradability is low, and also the kinetic viscosity is low and further because such end products as the lubricant which contain the (poly)alkylene glycol higher alkyl ether derivative composition is deprived of the general-purpose property. Since the kinetic viscocity of the composition can be controlled to a required level by suitably varying the addition mol number, n, of the AO, the range for the real number n is properly decided so that the control may permit selection of the kinetic viscosity optimum for the kind of end product for which the composition is intended. If the real number, n, exceeds 2, the oxyalkylene groups represented by AO may occur either singly or in the form of combination of two or more members. When these oxyalkylene groups occur in the form of a combination of two or more members, they are expected to total a real number, n, on average.

The letter, x, in the general formula (1) mentioned above represents 0 or 1. When x is 0, the relevant derivative is an ether derivative. When it is 1, the derivative is an ester derivative.

The letter, y, in the general formula (1) mentioned above represents a real number in the range of 1–10, preferably in the range of 1–4, on average. If the real number, y, exceeds 10, the composition will be at a disadvantage in betraying deficiency in lubricity and surface activity, exhibiting unduly high viscosity, suffering degradation of biodegradability, and incurring decline of kinetic viscosity.

The (poly) alkylene glycol higher alkyl ether derivative composition of this invention embraces an ether carboxylic acid derivative composition which has an alkylene group of 2–4 carbon atoms for A, a real number in the range of 1–20 on average for n, 0 for x, 1 for y, and $R^4COOM$ having an alkylene group of 1–4 carbon atoms for $R^4$ and a hydrogen atom, an alkali metal atom, an alkaline earth metal atom, an ammonium group, or an alkanol ammonium group for M for $R^3$ in the general formula (1) mentioned above.

Further, the (poly)alkylene glycol higher alkyl ether derivative composition of this invention embraces a diether derivative composition which has an alkylene group of 2–4 carbon atoms for A, 0 for x, 1 for y, and an alkyl group of 1–50 carbon atoms, a cycloalkyl group, an alkenyl group, or an aryl group for $R^3$ in the general formula (1) mentioned above.

The (poly)alkyleneglycol higher alkyl ether derivative composition of this invention further embraces a carboxylic ester derivative composition which has an alkylene group of 2–4 carbon atoms for A, 1 for x, a real number in the range of 1–4 on average for y, $R^5[COOM]_z$ having a hydrocarbon residue of 1–60 carbon atoms for $R^5$ and a hydrogen atom, an alkalimetal atom, an alkaline earth metal atom, an ammonium group, or an alkanol ammonium group for M for $R^3$, a real number in the range of 0–3 for z, and a real number in the range of 1–4 for y+z in the general formula (1) mentioned above.

The (poly)alkylene glycol higher alkyl ether derivative composition of this invention further embraces a hydroxycarboxilic ester derivative composition which has an alkylene group of 2–4 carbon atoms for A, 1 for x, 1 for y, and a residue resulting from the exclusion of a carboxyl group from a monohydroxymonocarboxylic acid of 10–24 carbon atoms or a residue resulting from the exclusion of a carboxyl group from a (poly)ester derived by the condensation of a monohydroxymonocarboxylic acid of 10–24 carbon atoms for $R^3$ in the general formula (1) mentioned above.

The aforementioned (poly)alkylene glycol higher alkyl ether derivative composition of this invention can be synthesized as by the following reaction.

For a start, a monoether (A) represented by the following general formula (2);

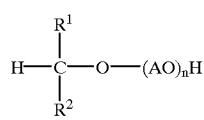

(2)

(wherein $R^1$, $R^2$, A, and n have the same meanings as defined above) by causing a long-chain olefin of 8–30 carbon atoms to react with a (poly)alkylene glycol in the presence of an acid catalyst and separating the reaction product by distillation, extraction, or other similar method.

The long-chain olefin to be used as one of the raw materials for the production of the monoether (A) is required to be a hydrocarbon comprising 8–30 carbon atoms and containing an ethylenically unsaturated bond and preferred to be a noncyclic hydrocarbon comprising 10–20 carbon atoms and containing an ethylenically unsaturated bond. As concrete examples of the long-chain olefin, octene, decene, dodecene, dodecene, tetradecene, hexadecene, octadecene, eicocene, dococene, tetracocene, hexacocene, octacocene, and triacocenes such as, for example, 1-decene, 2-decene, 1-dodecene, 2-dodecene, 3-dodecene, 4-dodecene, 5-dodecene, 1-tetradecene, 2-tetradecene, and 1-hexadecene maybe cited. Among other long-chain olefins mentioned above, decene, dodecene, tetradecene, hexadecene, octadecene, and eicocene proves particularly advantageous from the viewpoints of low-temperature flowability, lubricity, friction decreasing property, compatibility, release property, and surface activity. These long-chain olefins may be used either singly or in the form of amixture of two or more members.

These long-chain olefins may possess the unsaturated bond at the α position, at the inner position, or at the α position and the inner position as in the case of a mixture. They are not particularly descriminated on account of the position of the unsaturated bond. It is naturally allowable to use in combination two or more of such long-chain olefins which are different in the position of the unsaturated bond.

As concrete examples of the (poly)alkylene glycol to be used as one of the raw materials for the production of the monoether (A) mentioned above, monoethylene glycol, diethylene glycol, triethylene glycol, polyethylene glycol, monopropylene glycol, dipropylene glycol, tripropylene glycol, polypropylene glycol, 1,3-propane diol, 1,2-butane diol, 2,3-butanediol, 1,4-butanediol, 1,6-hexanediol, and 1,4-cyclohexane methane diol may be cited. Among other (poly)alkylene glycols mentioned above, monoethylene glycol, monopropylene glycol, 1,3-propane diol, 1,2-butane diol, 2,3-butane diol, and 1,4-butane diol may be rated as particularly advantageous from the viewpoints of reactivity, yield, and lubricity and surface activity of the produced (poly)-alkylene glycol higher alkyl ether derivative composition. These (poly)alkylene glycols may be used either singly or in the form of a mixture of two or more members.

The molar ratio of the (poly)alkylene glycol mentioned above to the long-chain olefin mentioned above, though not particularly limited, is generally in the range of 0.05–20, preferably in the range of 0.1–10. If this molar ratio is less than 0.05, the monoether (A) will be produced with a low yield. Conversely, if the molar ratio exceeds 20, the production of the monoether (A) will be at an economic disadvantage in requiring an addition to the inner volume of the reaction vessel. As respects the reaction conditions for the addition of the aforementioned (poly)alkylene glycol to the unsaturated bond of the long-chain olefin mentioned above, the reaction temperature is generally in the range of 50–250° C., preferably in the range of 100–200° C., and the reaction pressure, which may be reduced pressure, normal pressure, or increased pressure, is generally in the range of normal pressure –20 kg/cm². If the reaction temperature is less than 50° C., the rate of reaction will be unduly low. Conversely, if the reaction temperature exceeds 250° C., the reaction will be at a disadvantage in lowering the selectivity thereof by incuding such secondary reactions as polymerization of the long-chain olefin and decomposition and condensation polymerization of the (poly)alkylene glycol, for example.

As concrete examples of the acid catalyst to be used for the reaction of the long-chain olefin with the (poly)alkylene glycol, strongly acidic ion-exchange resins, crystalline aluminosilicates like BEA type zeolite, and dodecylbenzene-sulfonic acid may be cited. In terms of the reactivity, crystalline aluminosilicates prove preferable and the BEA type zeolite, among others, proves especially advantageous.

The proportion of the acid catalyst mentioned above to the long-chain olefin mentioned above is in the range of 1–50 wt. %, preferably in the range of 2–30 wt. %. If the proportion of the catalyst is less than 1 wt. %, the catalyst will not manifest an ability enough for promoting the addition reaction. Conversely, if the proportion exceeds 50 wt. %, the excess will be just wasted without bringing any proportionate addition to the effect of catalyst.

After the reaction, the catalyst is optionally separated and the reaction solution is then separated into an olefin phase and a (poly)alkylene glycol phase. The olefin phase is distilled to expel the unaltered olefin by vaporization and recover a monoether (A). Though the monoether (A) which remains after the separation of the unaltered olefin may be put to use in the subsequent cycle of the reaction, the recovered monoether (A) is preferred to be rectified before it is used. Though the conditions for this rectification cannot be generally specified because they vary with the starting material to be used. The rectification is required at least to effect removal of such impurities as olefin polymers which are by-produced during the reaction.

The addition reaction of the olefin and the (poly)alkylene glycol can be carried out in accordance with any of the methods of popular use such as the method for batchwise. reaction and the method for continuous reaction. When a batchwise reaction vessel is used, the reaction solution obtained at the end of one batch of reaction is optionally centrifuged or filtered to separate the catalyst therefrom and then subjected to the phase separation mentioned above. Subsequently, the monoether (A) aimed at is recovered from the olefin phase as by distillation. The unaltered raw materials can be used for the subsequent batch of reaction. When a continuous reaction vessel is used, the vessel may be any of the standard types such as the fluidized bed type, fixed bed type, and stirring tank type. The reaction is advanced and the unaltered raw materials are suitably circulated meanwhile to the reaction vessel. The separation of the catalyst and the recovery of te monoether (A) in this case are performed in the same manner as when the batch type reaction vessel is used.

The monoether (A), which is basically a monoether (a-1) obtained by the reaction of a long-chain oiefin of 8–30 carbon atoms with a (poly)alkylene glycol as described above, may be alternatively what is obtained by adding an alkylene oxide such as ethyelene oxide, propylene oxide, butylene oxide, or styrene oxide to the monoether (a-1) mentioned above. The monoether (a-2) which has the alkylene oxide added to the monoether (a-1) is obtained by adding the alkylene oxide to the monoether (a-1) in the presence of an alkali catalyst.

The number of addition mols of the alkylene oxide to the monoether (a-1) as the product mentioned above, though not particularly limited, is properly in the range of 1–299, preferably in the range of 1–199. If the number of addition mols of the alkylene oxide exceeds 299, the composition will be at a disadvantage in not aquiring the lubricity and surface activity as required because the number of addition mols, n, of the AO in the aforementioned general formuma (1) representing the monoether (a-1) exceeds the limit defined above.

As respects the reaction conditions for the further addition of the alkylene oxide to the aforementioned monoether (a-1), the reaction temperature is generally in the range of 50–250° C., preferably in the range of 100–200° C., and the reaction pressure which may be either normal pressure or increased pressure is generally in the range of normal pressure −20 kg/cm$^2$. If the reaction temperature is less than 50° C., the rate of reaction will become unduly low. Conversely, if the reaction temperature exceeds 250° C., the composition will be at a disadvantage in entailing aggravation of decomposition and increase in the amount of by-products.

The aforementioned alkali catalyst is the hydroxide of an element belonging to alkali metals or alkaline earth metals. As concrete examples of the alkali catalyst, sodium hydroxide, potassium hydroxide, lithium hydroxide, magnesium hydroxide, calcium hydroxide, and barium hydroxide may be cited. In terms of the ease of procurement and the magnitude of reactivity, sodium hydroxide, potassium hydroxide, etc. prove particularly preferable among other alkali catalysts mentioned above. The alkali catalyst may be used in a powdery state or a granular state in the reaction system or may be otherwise added in the form of an aqueous solution to the reaction system and continuously subjected to dehydration before use. The amount of the alkali catalyst to be used is generally in the range of 0.01–2.0 wt. %, preferably in the range of 0.02–0.5 wt. %, based on the amount of the alkoxylate as a raw material.

Thus, the monoether (A) mentioned above may be obtained as the monoether (a-1) and/or the (a-2) which is produced by the method described above. The monoether (A) mentioned above, therefore, can further embrace the monoether (a-1) obtained by adding the (poly)alkylene glycol to the double bond of the long-chain olefin and/or the monoether (a-2) obtained by further adding an alkylene oxide.

The monoether (A) as one of the raw materials for the (poly)alkylene glycol higher alkyl ether derivative composition requires to comprise 30–90 mol. %, preferably 40–80 mol. %, of the monoether (A1) having a methyl group for $R^1$ and 70–10 mol. %, preferably 60–20 mol. %, of the monoether (A2) having an alkyl group of not less than 2 carbon atoms for $A^1$. If the proportion of the monoether (A1) exceeds 90 mol. %, the ether or ester derivative to be described specifically below will be deficient in performance as a lubricant, a detergent, or a dermatologic medicine for external use. Conversely, if the proportion of the monoether (A1) is less than 30 mol. %, the composition will be at a disadvantage in not only inevitably admitting impurities by reason of manufacture to the extent of entailing a degradation in the performance thereof manifested as a lubricant, a detergent, or a dermatologic medicine for external use but also bringing such economic defects as increasing the cost of production because of an elongation of reaction time and a decline of productivity.

The production of the monoether (A) comprising the monoether (A1) and the monoether (A2) in the percentage ratio mentioned above, when 1-dodecene is used, for example, as the starting material olefin, has to be implemented by heating the 1-dodecene in the presence of an acid catalyst or a base catalyst by converting part of the 1-dodecene into inner dodecene and causing the resultant mixture of 1-dodecene and inner dodecene [in a ratio of 25:75 (mol. %), for example] to react with the (poly)alkylene glycol. Further, by using an α-olefin as one of the raw materials, the mixture of the α-olefin with an inner olefin can be obtained and, at the same time, the monoether (A) can be obtained by suitably selecting the reaction time because the reaction of isomerization of the olefin proceeds during the reaction of the α-olefin with the (poly)alkylene glycol. It is also allowable to use the α-olefin as the raw material, recover and circulate the unaltered inner olefin remaining after the reaction, and use the resultant mixture of the α-olefin with the inner olefin for the reaction. When the production is carried out by the method of this sort, the necessity for performing such onerous works as adjusting the composition ratio of the mixture after the production thereof may be obviated. Naturally, by separately producing a monoether containing the monoether (A1) in a proportion exceeding 90 mol. % and a monoether containing the monoether (A2) in a proportion of less than 30 mol. % and mixing them at a suitable ratio, the monoether (A) satisfying the composition ratio contemplated by this invention can be prepared.

In the (poly)alkylene glycol higher alkyl ether derivative composition of this invention, the ether carboxylic acid derivative composition mentioned above can be produced by a method which consists in causing a monoether (A) of the general formula (2) to react with a halogenated lower carboxylic acid or a salt thereof, a method which consists in subjecting the monoether (A) to liquid-phase oxidation in the presence of a catalyst of such precious metal as platinum or palladium, or a method which consists in adding the monoether (A) to acrylic acid or a derivative thereof or acrylonitrile.

Among other methods mentioned above, the method which resorts to the reaction of the monoether (A) with the halogenated lower carboxylic acid or a salt thereof is used particularly advantageously on a commercial scale. Thus, this method will be described below.

According to this method, the monoether (A) of the general formula (2) is caused to react with a monohalogenated carboxylic acid (salt) represented by the general formula (3):

X—R⁴—COOM                                      (3)

(wherein X represents a halogen atom and $R^4$ and M have the same meanings as defined above). Among other monohalogenated carboxylic acids (salts) of the general formula (3), monochlorinated carboxylic acids, especially monochloroacetic acid, are used particularly advantageously. The reaction, therefore, may be satisfactorily effected by mixing the monoether (A) with monochloroacetic acid thereby preparing a homogeneous solution and supplying an aqueous sodium hydroxide solution, generally an aqueous sodium hydroxide solution of a concentration in the approximate range of 40–50 wt. %, to the homogeneous solution under such conditions as a temperature in the range of 50–60° C. and a pressure reduced to a degree of 50 mmHg, for example. The molar ratio of the monoether (A), the monochloro-acetic acid, and the sodium hydroxide in this case, namely monoether (A)/monochloroacetic acid/ sodium hydroxide, is in the range of 1/0.9–1.1/1.8–2.2. After the completion of this reaction, the sodium salt of ether carboxylic acid is obtained by removing from the reaction solution the by-produced sodium chloride by such a method as filtration or centrifugation, for example.

The acid type ether carboxylic acid derivative composition of this invention is obtained satisfactorily by adding an aqueous solution of strong acid such as, for example, sulfuric acid or hydrochloric acid to the aforementioned sodium salt of ether-carboxylic acid, adjusting the resultant mixture to a pH of not more than 2, and separating the resultant free ether carboxylic acid derivative. It is allowable alternatively to obtain the ether carboxylic acid derivative composition by causing the aqueous solution of a sodium salt of ether carboxylic acid to contact a strongly acidic ion-exchange resin and inducing ion-exchange of sodium with hydrogen.

In using the ether carboxylic acid derivative composition of this invention as a detergent, for example, the composition ideally fits the detergent when it has an alkylene group of 2–4 carbon atoms for A, a real number of 1–20 on average for n, 0 for x, 1 for y, and $R^4COOM$ having an alkylene group of 1–4 carbon atoms for $R^4$ for $R^3$ in the general formula (1).

In the (poly)alkylene glycol higher alkyl ether derivative composition of this invention, the diether derivative composition mentioned above can be obtained by etherifying the terminal hydroxyl group of the monoether (A) of the general formula (2).

This etherification has no particular limit. It can be effected by using any of various methods which are available for etherification. For example, the method of Williamson Synthesis which comprises converting the monoether (A) mentioned above to a metal alcoholate as with an alkali metal or a caustic alkali and subsequently causing the metal alcoholate to react with a halogenated alkyl, a method which consists in adding the monoether (A) to an olefin in the presence of an acid catalyst, a method which consists in causing the monoether (A) to react with an alkyl sulfate, a method which consists in causing the monoether (A) to react with a dialkyl carbonate, and a method which consists in directly subjecting the monoether (A) and an alcohol to dehydrocondensation in the presence of an acid catalyst.

The aforementioned diether derivative composition of this invention thus obtained is the ether with a monohydric alcohol, i.e. the ether with a primary, secondary, or tertiary linear, branches, or cyclic alcohol of 1–50, preferably 1–30, carbon atoms, for example. As concrete examples of the monohydric alcohol of this description, methyl alcohol, ethyl alcohol, propyl alcohol, butyl alcohol, pentyl alcohol, hexyl alcohol, heptyl alcohol, octyl alcohol, nonyl alcohol, decyl alcohol, undecyl alcohol, dodecyl alcohol, tridecyl alcohol, tetradecyl alcohol, pentadecyl alcohol, hexadecyl alcohol, heptadecyl alcohol, octadecyl alcohol, nonadecyl alcohol, eicosyl alcohol, heneicosyl alcohol, docosyl alcohol, tricosyl alcohol, tetracosyl alcohol, cyclopentyl alcohol, cyclohexyl alcohol, vinyl alcohol, allyl alcohol, butenyl alcohol, pentenyl alcohol, phenyl alcohol, alkylphenyl alcohols, andbenzyl alcohol may be cited.

As concrete examples of the mono, di, and (poly) ethers with polyhydric alcohols other than (poly)alkylene glycols, polyhydric alcohols such as glycerin and 2–8mers thereof, trimethylol alkanes (trimethylol ethane, trimethylol propane, trimethylol butane, etc.) and 2–8mers thereof, pentaerythritol and 2–4mers, 1,2,4-butane triol, 1,3,5-penta-triol, 1,2,6-hexane triol, 1,2,3,4-butane tetrol, sorbitol, sorbitan, sorbitol glycerin condensate, adonitol, arabitol, xylitol, and mannitol; and ethers with such saccharides as xylose, arabinose, ribose, rhamnose, glucose, fructose, galactose, mannose, sorbose, cellobiose, maltose, isomaltose, trehalose, and sucrose may be cited. The ethers with polyhydric alcohols embrace those of the structure having all the hydroxyl groups of polyhydric alcohol etherified with the monoether (A) and those of the structure having part thereof etherified with the monoether (A) as well. The part of hydroxyl groups which have escaped the etherification are regarded as substituents in $R^3$ of the general formula (1).

When the aforementioned diether derivative composition of this invention is used as a lipophilic lubricant, an ether with a monohydric alcohol of 4–50, preferably 8–30, carbon atoms is suitable. When it is used as a hydrophilic lubricant or surfactant, an ether with a monohydric alcohol of 1–8, preferably 1–4, carbon atoms or an ether of a polyhydric alcohol with a partially etherified ether is suitable.

In the (poly)alkylene glycol higher alkyl ether derivative composition of this invention, the aforementioned carboxylic ester derivative composition is obtained by causing the monoether (A) of the general formula (2) to react with a carboxylic acid (monocarboxylic acid dicarboxylic acid, and polycarboxylic acid) represented by the general formula (4):

$R^3$—(COOH)$_y$                                      (4)

(wherein $R^3$ and y have the same meanings as defined above), an alkyl ester thereof, or an anhydride thereof. When a monocarboxylic acid is used, for example, y is 1 in the general formula (1). When a discarboxylia acid is used, y is 1 or 2 in the general formula (1).

As concrete examples of the carboxylic acid of the general formula (4), alkyl carboxylic acids, cycloalkyl carboxylic acids, alkenyl carboxylic acids, cycloalkenyl carboxylic acids, and dicarboxylic acids and polycarboxylic acids corresponding thereto may be cited.

As typical examples of the alkyl carboxylic acids, acetic acid, propionic acid, butyric acid, succinic acid, and adipic acid may be cited. As typical examples of the cycloalkyl carboxylic acids, cyclopentane carboxylic acid, cyclohexane carboxylic acid, and cycloheptane carboxylic acid may be cited. As typical examples of the alkenyl carboxylic acid, acrylic acid, methacrylic acid, and maleic acid may be cited. As typical examples of the cycloalkenyl carboxylic acid, dimer acids and trimer acids may be cited. As typical examples of the aryl carboxylic acid, benzoic acid and phthalic acid may be cited.

The expression "alkyl ester of general formula (4)" as used herein means a lower (1–4 carbon atoms) alkyl esters of the aforementioned carboxylic acids. As typical examples of the alkyl ester, methyl acetate, ethyl acetate, methyl propionate, methyl acrylate, ethyl acrylate, methyl methacrylate, and ethyl methacrylate may be cited.

The expression "anhydride of the general formula (4)" as used herein means the anhydrides of the carboxylic acids mentioned above. As typical examples of the anhydride, acetic anhydride, succinic anhydride, maleic anhydride, and phthalic anhydride may be cited.

The reaction of esterification mentioned above can be carried out by using a known acid or base catalyst. As concrete examples of the catalyst which is advantageously used, sulfuric acid, paratoluenesufonic acid, sodium hydroxide, potassium hydroxide, and sodium methylate; the oxides of titanium, tin, lead, zirconium, etc. represented by titanium oxide, tetramethoxy titanium, zinc oxide, dibutlyl tin oxide, dibutyl tin dilaurate, lead oxide, dimethoxy lead, and zirconium oxide and organic metal complexes may be cited. The amount of this catalyst to be used is generally in the range of 0.01–10 wt. %, preferably in the range of 0.1–5 wt. %, based on the total amount of the monoether (A) and the carboxylic acid. The reaction temperature is generally in the range of 50–220° C., preferably in the range of 80–200° C. The reaction pressure may be either reduced pressure or normal pressure and can be suitably decided, depending on the raw materials. The reaction solvent may used or may not be used. When a carboxylic acid is used as one of the raw materials, toluene, xylene, cyclohexane, or other similar organic solvent may be used for the purpose of promoting the dehydroesterification.

The ratio of the monoether (A) and the carboxylic acid of the general formula (4), an alkyl ester, or an acid anhydride thereof does not need to be particularly limited but may be suitably deciced. In the case of esterifying a monocarboxylic acid with the monoether (A), for example, these two compounds are generally used in their nearly equimolar weights.

Now, the aforementioned carboxylic acids will be described more specifically below. They are optionally substituted carboxylic acids of 1–60 carbon atoms. They may be linear type, branched type, cyclic type, or aromatic type and may be saturated or unsaturated. They may be monobasic acids or polybasic acids. They may contain such substituents as hydroxyl groups. As concrete examples of carboxylic acids of this description, saturated fatty acids such as methanoic acid (formic acid), ethanoic acid (acetic acid), propanoic acid (propionic acid), butanoic acid (butyric acid), pentanoic acid (valeric acid), hexanoic acid (caproic acid), heptanoic acid, octanoic acid (caprilic acid), nonanoic acid, decanoic acid (capric acid), undecanoic acid, dodecanoic acid (lauric acid), tridecanoic acid, tetradecanoic acid (myristic acid), pentadecanoic acid, hexadecanoic acid (palmitic acid), heptadecanoic acid, octadecanoic acid (stearic acid, isostearic acid, etc.), nonadecanoic acid, eicosanoic acid, heneicosanoic acid, docosanoic acid, tricosanoic acid, and tetracosanoic acid; unsaturated fatty acids containing one double bond such as propenoic acid (acrylic acid), butenoic acid (methacrylic acid, crotonic acid, etc.), pentenoic acid, hexenoic acid, heptenoic acid, octenoic acid, nonenoic acid, decenoic acid, undecenoic acid, tridecenoic acid, tetradecenoic acid, pentadecenoic acid, hexadecenoic acid, heptadecenoic acid, octadecenoic acid (oleic acid), nonadecenoic acid, eicosenoic acid, heneicosenoic acid, docosenoic acid, tricosenoic acid, and tetracosenoic acid; unsaturated fatty acids containing a plurality of double bonds such as linolic acid and linolenic acid; saturated dibasic acids such as ethanedioic acid (oxalic acid), propanedioic acid (malonic acid), butanedioc acid (succinic acid), pentanedioic acid, hexanedioic acid (adipic acid, etc.), heptanedioic acid, octanedioic acid, nonanedioic acid, decanedioic acid, undecanedioic acid,dodecanedioic acid, tridecanedioic acid, tetradecanedioic acid, pentadecanedioic acid, and hexadecanedioic acid; unsaturated dibasic acids such as butenedioic acid (maleic acid, etc.), pentenedioic acid, hexanedioic acid, heptenedioic acid, octenedioic acid, nonenedioic acid decenedioic acid, undecenedioic acid, dodecenedioic acid, tridecenedioic acid, tetradecenedioic acid, pentadecendioic acid, and hexadecenedioic acid; cyclic fatty acids such as dimer acids, trimer acids, and cyclopentanecarboxylic acid; aromatic carboxylic acids such as benzoic acid, salicylic acid, phthalic acid, terephthalic acid, trimellitic acid, pyromellitic acid, and naphthoic acid; hydroxy acids such as glycolic acid, lactic acid, hydroxybutyric acid, hydroxyvaleric acid, ricinolic acid, hydroxystearic acid, citric acid, tartaric acid, gluconic acid, and malic acid, and (poly) esters resulting from condensation thereof (possessed of a carboxyl group at the terminals) may be cited. The esters with polybasic acids may be monoesters, diesters, or polyesters in structure. The carboxylic acids that are not esterified may be acid type or salt type. These partly unesterif ied carboxyl groups are recognized as substituents in $R^3$ of the general formula (1).

In this invention, when y in the general formula exceeds 1, x may be 0 or 1, whichever better suits the occasion. In other words, the ether derivative and the ester derivative of the monoether (A) are both present in the molecular unit of the composition. Specifically, the derivative obtained by further esterifying the carboxylic acid site of the ether carboxylic acid derivative of this invention with the monoether (A) and the derivative obtained by further etherifing the hydroxyl group of a hydroxycarboxylic ester (such as hydroxystearic acid) of the monoether (A) with the monoether (A) are examples.

This invention allows the substituent, $R^3$, in the general formula (1) to be a hydroxyl group or a carboxyl group. It further embraces the substituent that results from etherifying or esterifying the substituent just mentioned. Specifically, a derivative constructed by etherifying a hydroxyl group with an alcohol other than the monoether (A), a derivative constructed by effecting the esterification with a carboxylic acid, and a derivative constructed by esterifying a carboxyl group with an alcohol other than the monoether (A) are embraced.

In the aforementioned carboxylic ester derivative compositions of this invention, particularly those obtained by homopolymerizing such polymerizing monomers as acrylic ester, methacrylic ester, and maleic ester or by copolymerizing them with various monomers can be utilized in the field of coating material, adhesive agent, resin, plastic, macromolecular surfactant (dispersion or emulsification), viscosity index enhancer, pour depressant, and gelling agent. Such compositions as phthalic esters can be advantageously utilized as solvent and plasticizer.

In the (poly)alkylene glycol higher alkyl ether derivative composition of this invention, particularly that which comprises 40–80 mol. % of the (B1) derivative and 60–20 mol. % of the (B2) derivative proves advantageous.

The (poly) alkylene glycol higher alkyl ether derivative composition of this invention can be used as detergent, lubricant, dermatologic medicine for external use, solvent, plasticizer, and polymerizing monomer.

(1) Detergent

The range of the (poly)alkylene glycol higher alkyl ether derivative composition of this invention which proves preferable for use as a detergent has a real number of 1–50, preferably 1–30, for n and the oxyethylene group, AO, rather has a large content. To be specific, when the number of species of oxyalkylene group is not less than 2, the content of the oxyethylene (EO) group is not less than 50 mol. %, preferably not less than 70 mol. %, based on the total amount of oxyalkylene groups. $R^3$ represents an organic residue having not more than 8 carbon atoms, preferably not more than 4 carbon atoms. A composition having a carboxyl group and a hydroxyl group as substituents is suitable as a detergent without reference to the EO content and the number of addition mols of AO. If the upper limit of the range is exceeded, the composition will be at a disadvantage in lowering water-solubility and other similar properties of a detergent. In the compositions, the ether carboxylic acid (salt) derivative composition mentioned above is suitably used as a foaming detergent and the methyl ether derivative composition is suitably used as a sparingly foaming detergent.

When the (poly)alkylene glycol higher alkyl ether derivative composition of this invention is used as a detergent, it is preferred to comprise 30–90 mol. % of the (B1) derivative having a methyl group for $R^1$ and 70–10 mol. % of the (B2) derivative having an alkyl group of not less than two carbon atoms for $R^1$ respectively in the general formula (1), preferably 40–80 mol. % of the (B1) derivative and 60–20 mol. % of the (B2) derivative to be suitably used as the detergent. The (poly)alkylene glycol higher alkyl ether derivative composition which comprises the (B1) derivative and the (B2) derivative in a ratio falling in the range mentioned above particularly manifests an excellent deterging property.

The detergent of this invention contains the (poly) alkylene glycol higher alkyl ether derivative composition mentioned above in an effective amount, generally in a concentration in the range of 3–60 wt. %. The (poly)alkylene glycol higher alkyl ether derivative composition af this invention can be used in combination with other known surfactant such as, for example, primary alcohol alkoxylate, secondary alcohol alkoxylate, anionic surfactant, cationic surfactant, or alkanol amine.

As concrete examples of the primary alcohol alkoxylate, higher primary alcohol alkoxylates having ethylene oxide or ethylene oxide and propylene oxide added in a proportion of 5–30 mols on average to a primary alcohol of 8–20 carbon atoms may be cited. These higher primary alcohol alkoxylates can be used either singly or in the form of a mixture of two or more members.

As concrete examples of the higher secondary alcohol alkoxylate, alkoxylates having ethylene oxide or ethylene oxide and propylene oxide added in a proportion of 3–20 mols on average to a secondary alcohol of 8–20 carbon atoms and alkoxylates having an alkylene glycol added to an olefin of 8–30 carbon atoms and then having ethylene oxide or ethylene oxide and propylene oxide further added in a proportion of 3–20 mols to the resultant addition product may be cited. These alkoxylates can be used either singly or in the form of a combination of two or more members.

As concrete examples of the anionic surfactant, alkyl sulfonates of 10–18 carbon atoms, alkane sulfonates of 10–18 carbon atoms, olelin sulfonates of 10–18 carbon atoms, alkyl-benzene sulfonates containing an alkyl group of 10–18 carbon atoms, andalkyl (or alkenyl) polyethoxy sulfonates containing an alkyl group or alkenyl group of 10–18 carbon atoms (the ethylene oxide having an average number of added mols: 2–7) may be cited. The term "sulfonate" mentioned above means alkali metal salts, alkaline earth metal salts, ammonium salts, and alkanol amine salts. These anionic surfactants may be used either singly or in the form of a combination of two or more members.

As concrete examples of the cationic surfactant, quaternary ammonium salts, imidazolium salts, and more specifically monoalkyl (C6–C24) trimethyl ammonium salts may be cited. These cationic surfactants may be used either singly or in the form of a combination of two or more members.

As concrete examples of the alkanol amine, alkanol amines such as monoethanol amine, diethanol amine, triethanol amine, monopropanol amine, dipropanol amine, and tripropanol amine and fatty acid amides of such alkanol amines may be cited. These alkanol amines may be used either singly or in the form of a combination of two or more members.

The detergent of this invention may incorporate therein various additives which are generally used in a detergent composition, depending on the kind of use and the purpose of use. As concrete examples of such additives, foam enhancers such as polyoxyethylene alkyl ethers and fatty acid alkanol amides, hydrotrop agent such as lower alcohol, polyhydric alcohol, polyethylene glycol, and lowly arylsulfonic acid, sequestering agents such as ethylenediamine tetraacetic acid, diethylene triamine pentaacetic acid, citric acid, and metal salts thereof, mildewproofing agents such as benzoic acid, pigment, perfume, alkali agents, polishing agents, bleaching agents, and enzymes may be cited.

The (poly)alkylene glycol higher alkyl ether derivative composition of this invention can be used as nonionic surfactant, anionic surfactant, active components for industrial grade detergent, household detergents for clothes, detergents for kitchen use, and shampoos, and for emulsifiers and suspending agents. Further, the detergent composition of this invention can be used for industrial grade and household grade detergents. These end products can be used in various forms such as powder, paste, and liquid.

(2) Lubricant

As the lubricant contemplated by this invention, the (poly)alkylene glycol higher alkyl ether derivative composition can be used in its unmodified form or, when necessary, as mixed with such conventionally known lubricant as mineral oil (petroleum type lubricant oil) or synthetic oil (synthetic lubricant oil) in a proper ratio. The term "conventionally known mineral oil" as used herein means a lubricant oil manufactured from petroleum. Though the physical attributes and properties of this lubricant oil are largely affected by the composition of the paraffin type, aromatic type, and alicyclic type (naphthene type), the lubricant oil is basically a complicated mixture of hydrocarbon molecules and these components range from a component of low viscosity having an approximate molecular weight of 250 to a component of very high viscosity having an approximate molecular weight of 1000. As concrete examples of the synthetic oil (synthetic lubricant oil), polyolefins such as poly-α-olefin and polybutene; silicones such as dimethylsilicones; polyol esters such as pentaerythritol ester, and trimethylol propane ester; polyalkylene glycols such as polyethylene glycol and polypropylene glycol; silicic esters such as tetradecyl silicate and tetraoctyl silicate; diesters such as DIDA, DOA, and DOS; polyphenyl ethers such as polyphenyl ether; phosphoric esters such as propylphenyl phosphate and TCP; alkyL aromatics such as alkyl benzene; alkyl naphthenes such as 2,4-dicyclohexyl-2-methyl pentane; and fluorinated hydrocarbons may be cited.

The lubricant of this invention, when necessary, may further incorporate therin such additives as load-resisting additives, pressureproofing agents, antioxidants, rustproofing agents, detergent-dispersants, pour depressants, viscosity index enhancers, defoaming agents, wear resisting agents, and gelling agents. The ratio of incorporation of these additives is not particularly limited. These additives are only required to be suitably contained so much as to manifest their qualities thoroughly, depending on the purposes for which they are used. As concrete examples of the antioxidant, chain terminators such as hindered phenols (such as 2,6-di-t-butyl-p-cresol) and aromatic amines (such as phenyl-α-naphthyl amine), peroxide decomposers such as dialkyl or diaryl zinc dithiophosphate, dialkyl dithiocarbamate, sulfur compounds (such as terpene sulfide), and dialkyl selenade, and metal inactivating agents such as 2,5-dimercapto-1,3,4-thiaziasole, and bezotriazole may be cited. Preferably, they can be added in a proportion in the range of 0.01–20 wt. %. As concrete examples of the detergent additive, alkaline earth metal (Ca, Mg, and Ba) salts of petroleum sulfonic acid, alkylbenzene sulfonic acid, alkylphenol sulfide, alkylphosphoric acid, petroleum naphthenic acid, and alkyl salicylic acid, metallic detergents such as are obtained by dispersing about 10 mols of fine particles of a carbonate in 1 mol of the aforementioned neutral basic salt thereby imparting acid neutrality to the resultant dispersion, and ashless dispersants of polybutenyl imide succinate, polybutenyl hydroxybenzyl amine, and amides of isostearic acid with polyamine may be cited. Preferably, they may be added in a propirtion in the range of 0.5–30 wt. %. As concrete examples of the pressure resisting agent and the wear resisting agent, sulfur compounds such as sulfide whale brain oil, dibenzyl disulfide, and prefin polysulfide, phosphorus compounds such as tricresyl phosphate, tributyl phosphite, and lauryl amine salt of phophorous acid, chlorine compounds such as chlorinated paraffin, organic metal compounds such as zinc naphthenate and dialkyl or diaryl zinc dithiophosphate, and potassium borate dispersion may be cited. Preferably, they may be added in a proportion in the range of 0.5–10 wt. %. As concrete examples of the oily agent and the friction correcting agent, fatty acids (such as oleic acid and stearic acid), fatty oils (such as beef tallow and port lard), oily agents such as long-chain alcohols (such as lauryl alcohol), and friction adjusting agents such as dialkyl molybdenum dithiophosphate, half esters of polyhydric alcohols, amines, amides, and sulfide esters may be cited. Preferably, they may be added in a proportion in the range of 0.1–2.0 wt. %. As concrete examples of the viscosity index enhancer, polyalkyl methacrylate (molecular weight 10,000–1,000,000), dispersion type polyalkyl methacrylate (copolymerized with such polar monomers as N-vinyl pyrrolidone), polyisobutylene (molecular weight 5,000–300,000), ethylene-propylene copolymers (molecular weight 20,000–100,000), and styrene-diene copolymer hydrides (molecular weight 20,000–100,000) may be cited. Preferably, they may be added in a proportion in the range of 0.5–30 wt. %. As concrete examples of the pour depressant, polyalkyl methacrylate (concurrently serving as viscosity index enhancer), chlorinated paraffin-naphthalene condensate, and alkylated polystyrene may be cited. Preferably, they may be added in a proportion in the range of 0.1–5.0 wt. %.

It is important that the lubricant of this invention be selected, in due consideration of the purpose of use, the shape and material of a part fated to be worn, and such lubrication conditions as load, rate, and atmosphere, so as to fulfill at least such conditions that (1) the liquid lubricant should possess a proper viscosity in the range of working temperatures or the grease should possess a proper consistency, (2) the lubricant should possess a boundary lubrication quality fit for the intended use, (3) the lubricant should be stable to withstand heat and oxidation, and (4) the lubricant should contain no foreign matter and further fulfill and optimize such properties as have been strongly demanded heretofore in the relevant uses. These conditions are attained by adjusting the (poly)alkylene glycol higher alkyl ether derivative composition and the compositions of the additives. Specifically, the lubricant can be arbitrarily manufactured in varying types, ranging from the type which flows at room temperature to the type which resembles a brick so hard as to be cut with a knife. Such metal working oils as hydraulic fluid, cutting oil, and rolling oil, for example, which fit high speed works for which generally cooling property or fire resistance constitute an important consideration are possibly used in the form of an aqueous liquid such as aqueous solution or emulsion containing not less than 5% of additives and not less than about 30% of water, the cutting oils which fit cutting works performed at relatively low speed and fated to be affected by abrasion are possibly used in an oily form containing a sulfur and chlorine pressure-resisting agent, and metal working oils which fit the work of rolling, drawing, and other molding are possibly used in the form of oil-water emulsion (the emulsion obtained by emulsifying a metal working base oil containing the (poly)alkylene glycol higher alkyl ether derivative composition with a suitable surfactant) or in-the form of oil obtained by blending a lubricant containing (poly)alkylene glycol higher alkyl ether derivative composition with a suitable solid lubricant heretofore known to the art.

Since the lubricant of this invention is enabled to manifest required properties (such as, for example, fine thermal stability, low-temperature flowability, lubricity, wear reducing property, compatibility, release property, and biodegradability) by suitably selecting the kind and composition ratio of the (poly)alkylene glycol higher alkyl ether derivative composition, depending on the purpose of use, it is at an advantage in keeping from such detriments as being suddenly oxidized on reaching a temperature in the range of 100–120° C. as in the case of mineral oil, becoming unusable on account of increase of viscosity and separation of wax on being cooled to a level in the range of −20–−30° C., or becoming unserviceable in an application compelling expulsion on account of the absence of biodegradability.

The lubricant of this invention can be suitably utilized in a very wide range of applications in which such lubricants as mineral oil and synthetic oil have been heretofore used. It can be applied more advantageously particularly to the field which is in need of a lubricant excelling in such properties as thermal stability, low temperature flowability, lubricity, wear reducing property, compatibility, release property, and biodegradability which the conventional lubricating oil has not manifested fully satisfactorily and which have remained yet to be improved. To be specific, it can be used particularly advantageously as added to automobile lubricant oils such as two-cycle and four-cycle engine lubricant oils and other similar engine oils, gear oils, automatic transmission oils, and brake oils, marine lubricating oils such as system oils, cylinder oils, and diesel engine oils; industrial lubricating oils such as industrial gear oils, bearing oils, turbine oils, and other similar machine lubricating oils, metal working oils such as hydraulic fluids, (air) compressor oils, slide guide face lubricating oils, rolling oils, cutting oils, polishing oils, and press working oils, industrial lubricating oils such as refrigerator oils, machine oils, electric insulating oils, heat-treating oils, and rust preventing oils; and extrusion molding lubricating oils and resin molding lubricating oils for use as compression molding release agents.

The lubricating agent of this invention has been described with respect to the requirements for construction. Now, the uses found for typical examples of the lubricating agent will be described below with respect to the optimum requirements that satisfy the functions which are required of the lubricating agent.

(a) Engine oils, machine oils, refrigerator oils, textile processing lubricant agents, and resin molding lubricating agents.

When the lubricating agent of this invention is used for an engine oil, machine oil, refrigerator oil, textile processing lubricating agent, or resin molding lubricating agent, the primary condition for obtaining a satisfactory lubricating proerty consists in maintaining fluid lubricity. For the maintenance of fluid lubricity, viscosity constitutes itself an important factor. The viscosity of the lubricating agent is defined by the kinetic viscosity at 40° C. Properly, the kinetic viscosity of the lubricating atent is in the range of 1–30000 $mm^2/s$, preferably in the range of 5–20000 $mm^2/s$. If the kinetic viscosity of the lubricating agent at 40° C. is less than 1 $mm^2/s$, the lubricating agent will be deficient in lubricity. Conversely, if the kinetic viscosity at 40° C. exceeds 30000 $mm^2/s$, the lubricating agent will be deficient in flowability.

The number of addition mols of the alkylene oxide (the number of addition mols of the AO in the general formula (1)) of the (poly)alkylene glycol higher alkyl ether derivative composition which fits the lubricating agent under discussion is in the range of 1–300. If the number of addition mols, n, exceeds 300, the (poly)alkylene glycol higher alkyl ether derivative composition will be at a disadvantage in not acquiring the kinetic viscosity defined above and incurring difficulty in maintaining the required fluid lubricity. The (poly)alkylene glycol higher alkyl ether derivative composition, therefore, is allowed to have the alkylene oxide unit [AO in the general formula (1)] consist solely of one species, i.e. oxyethylene group (hereinafter occasionally referred to briefly as "EO"), oxy-propylene group (hereinafter occasionally referred to briefly as "PO"), or oxybutylene group (hereinafter occasionally referred to briefly as "BO"), or comprise two or more such spacies. When the composition comprises two or more species, it may be a random copolymer of two or more species of oxyalkylene group or a block copolymer of such species.

In the (poly)alkylene glycol higher alkyl ether derivative composition which fits the lubricating agent, the lubricity of the composition generally becomes better but the biodegradability thereof becomes worse in proportion as the ratio of the units, PO and BO, increases. For the sake of enabling the composition to manifest satisfactory compatibility with the mineral oil or the refrigerator coolant, therefore, it is advantageous to use the composition which results from copolymerizing PO and BO. The biodegradability of the composition is improved and the water solubility thereof is enhanced in accordance as the EO unit is increased.

The number of addition mols of oxyalkylene group in the (poly)alkylene glycol higher alkyl ether derivative composition defined as described above may be properly selected within the range so as to suit the kind of use and the purpose of use of the lubricating agent. Since the kinetic viscosity is increased by increasing the number of addition mols, n, of the AO in the general formula (1), the number of addition mols of the oxyalkylene group can be promptly decided by taking into account the relation.

The (poly)alkylene glycol higher alkyl ether derivative composition is preferred to be an ether derivative or an ester derivative. In the general formula (1), $R^3$ has not less than four carbon atoms, preferably not less than eight carbon atoms. An ether derivative with a monohydric aocohol of 4–30 carbon atoms, an ester derivative with a monovalent carboxylic acid of 4–30 carbon atoms, and an ester derivative with a polyvalent carboxylic acid of 4–60 carbon atoms may be cited as concrete examples. Ester derivatives with a dimer acid or a trimer acid may be also cited as preferable derivatives. Further, ester derivatives with a hydroxy acid such as hydroxystearic acid and ester derivatives with a condensate of hydroxystearic acid may be also cited as preferred examples of the (poly)alkylene glycol higher alkyl ether derivative composition. The (poly)alkylene glycol higher alkyl ether derivative compositions which fall in the range mentioned above manifest a particularly excellent lubricating property.

When the (poly)ilkylene glycol higher alkyl ether derivative composition is used as a lubricating agent, it is particularly advantageously used in a configuration which comprises 30–90 mol. % of the (B1) derivative having a methyl group for $R^1$ and 70–10 mol. % of the (B2) derivative having an alkyl group of not less than two carbon atoms for $R^1$, preferably 40–80 mol. % of the (B1) derivative and 60–20 mol. % of the (B2) derivative, in the general formula (1). The (poly)alkylene glycol higher alkyl ether derivative composition which comprises the (B1) derivative and the (B2) derivative in a ratio in the aforementioned range manifests a particularly excellent lubricating property.

The lubricating agent of this quality, when necessary, is mixed with known mineral oil and synthetic oil such as poly-α-olefin in a suitable retio besides the (poly)alkylene glycol higher alkyl ether derivative composition.

Further, the lubricating agent of this quality, when necessary, is mixed with various known additives such as load resisting additive, pressure resisting agent, antioxidant, rust preventives, detergent additives, pour depressant, viscosity index enhancer, and defoaming agent.

(b) Metal Working Oils

When the lubricating agent of this invention is used as a metal working oil, the number of addition mols of an alkylene oxide of the (poly)alkylene glycol higher alkyl ether derivative composition which fits the lubricating agent [the number of addition mols, n, of the AO in the general formula (1)] is in the range of 1–100, preferably 1–70. If the number of addition mols, n, exceeds 100, the composition will be at a disadvantage in incurring difficulty in keeping the liquid lubricity favorable.

Particularly when the lubricating agent is used as a water-soluble metal working oil, the content of the oxyethylene group (EO) of the composition, i.e. the AO in the general formula (1), is required to be as large as possible. Specifically, when two or more species of the oxyalkylene group are used, the unit (content) of the oxyethylene group is preferred to be not less than 50 mol. %, preferably not less than 70 mol. %, based on the total amount of the oxyalkylene group. The number of addition mols of the alkylene oxide [the number of addition mols, n, of AO in the general formula (1)] is in the range of 3–100, preferably 5–70. If the number of addition mols, n, is less than 3, the composition will be at a disadvantage in lowering the water solubility. Conversely, if the number of addition mols, n, exceeds 100, the composition will be at a disadvantage in incurring difficulty in keeping the liquid lubricity fully satisfactory.

The (poly)alkylene glycol higher alkyl ether derivative composition is preferred to be an ether derivative, an ester derivative, or an ether carboxylic acid (salt) derivative. In the general formula (1), $R^3$ has not more than eight carbon atoms, preferably not more than four carbon atoms. Ether derivatives with a monohydric alcohol or a polyhydric alcohol of 1–8 carbon atoms and ester derivatives with a monovalent carboxylic acid or polyvalent carboxylic acid of 1–8 carbon atoms may be cited as examples.

The derivatives of the ranges mentioned above excel in water solubility and manifest excellent lubricating property.

When the lubricating agent is used as a metal working oil not dilutable with water or a hydrophobic metal working base oil (which may be emulsified into an emulsion by the use of a suitable surfactant), the content of the oxyethylene (EO) group, i.e. the AO in the general formula (1), is preferred to be small, the number of addition mols of EO to be small, and the PO or BO to be added. To be specific, when not less than two species of the oxyalkylene group are used, the unit of (EO) of the oxyethylene group is not more than 50 mol. %, preferably not more than 30 mol. %, of the total amount of the oxyelkylene group and the number of addition mols of EO is not more than 10 mols, preferably not more than 5mols.

The (poly)alkylene glycol higher alkyl ether derivative composition is preferred to be an ether derivative or an ester derivative. In the general formula (1), $R^3$ has not less than four carbon atoms, preferably not less than eight carbon atoms. Ester derivatives with a monohydric alcohol of 4 to 30 carbon atoms, ester derivatives with a monovalent carboxylic acid of 4–30 carbon atoms, and ester derivatives with a polyvalent carboxylic acid of 4–60 carbon atoms may be cited as examples. Ester derivatives with a dimer acid or trimer acid may be cited as preferable examples of the derivatives. Further, ester derivatives with a hydroxy acid such as hydroxy stearic acid and ester derivatives with a condensate with a hydroxy stearic acid may be cited as preferable examples of the (poly)alkylene glycol higher alkyl ether derivative composition. The metal working oil not diluted with water and the hydrophobic metal working base oil mentioned above are particularly suitable as the metal working oil agent which is insoluble in water.

When the (poly)alkylene glycol higher alkyl ether derivative composition of this invention used as a metal working oil, it can be used particularly advantageously in a configuration which comprises 30–90 mol. % of the (B1) derivative having a methyl group for $R^1$ and 70–10 mol. % of the (B2) derivative having an alkyl group of not less than two carbon atoms for $R^1$, preferably 40–80 mol. % of the (B1) derivative and 60–20 mol. % of the (B2) derivative, in the general formula (1). The (poly)alkylene glycol higher alkyl ether derivative composition which comprises the (B1) derivative and the (B2) derivative in a ratio in the aforementioned range manifests a particularly excellent lubricating property.

The advantageous requirements for adopting the lubricating agent of this invention for typical applications have been described. In addition to the applications shown above, the lubricating agent of this invention can be utilized as lubricating agents for magnetic recording materials and lubricating agents for precision machines. Since this lubricating agent abounds in solubility (compatibility) and plasticity, it can be also utilized as lubricating agents for inks and coating materials, and plasticizers for resins and plastics.

(3) Dermatologic Medicine for External Use

The (poly)alkylene glycol higher alkyl ether derivative composition of this invention can be utilized as dermatological medicines for external use such as base oils as sufactants in dermatological medicines for external use. When the (poly)alkylene glycol higher alkyl ether derivative composition to be contained in the dermatological medicine for external use is used as a base oil not soluble in water, the content of the oxyethylene group (EO) based on the total amount of the oxyalkylene group [AO in the general formula (1)] is not more than 50 mol. %, preferably not more than 30 mol. % and the number of addition mols of the EO is not more than 10 mols, preferably not more than 5 mols. In this case, the (poly)alkylene glycol higher alkyl ether derivative composition is preferred to be an ether derivative or an ester derivative. In the general formula (1), $R^3$ is preferred not to contain a substituent. Ether derivatives with a monohidric alcohol and ester derivatives with a monovalent carboxylic acid are used advantageously. $R^3$ is preferred to have 1–30 carbon atoms. The base oil is enabled to be deprived of solubility in water by selecting a derivatve having a large number of carbon atoms for $R^3$ without reference to the content of the oxyethylene group. In this case, it suffices to use an ether derivative or an ester derivative having 8–60, preferably 10–30, carbon atoms for $R^3$. By selecting the EO content in the total amount of AO and the number of mol additions of EO, or selecting the kind of derivative, the dermatological medicine for external use containing the base oil insoluble in water is enabled to excel in low stimulating property, low odor, proper viscosity, and compatibility with other oil-soluble components, and solubility. When the preferred range mentioned above is faithfully observed, the characteristic properties of the dermatological mdeicine for external use containing the water-insoluble base oil will be manifested more conspicuously.

When the (poly)alkylene glycol higher alkyl ether derivative composition contained in the dermatological medicine for external use of this invention is used as a surfactant, it suffices to control the HLB (hydrophilicity lipophilicity ratio) (the use of a surfactant having an HLB in the approximate range of 8–18 tends for form an O/W type emulsion and the use of a surfactant having an HBL in the approximate range of 3–6 tends to form a W/O type emulsion), depending on the purpose such as, for example, (1) the case of emulsifying an oil component in water as in cream or latex [oil-in-water (O/W) type emulsion], (2) the case of emulsifying water in an oil component (W/O type emulsion), (3) the case of solubilizing perfume and oily component in water as in lotion, and (4) the case of dispersing a pigment in water or an oily component as in foundation. Here, for the purpose of heightening the HLB (increasing the proportion of hydrophilicity), it suffices to heighten the number of addition mols of the oxyethylene group (EO) based on the total amount of the oxyalkylene group [AO in the general formula (1)] of the (poly)alkylene glycol higher alkyl ether derivative composition. In this case, the (poly)alkylene glycol higher alkyl ether derivative composition is preferred to be an ether derivative or an ester derivative. In the general formula (1), $R^3$ has not more than eight carbon atoms, preferably not more than four carbon atoms. Ether derivatives with a monohydric alcohol or polyhydric alcohol of 1–8 carbon atoms and ester derivatives with a monovalent carboxylic acid or polyvalent carbon acid of 1–8 carbon atoms may be cited as examples. The HLB can be heightened by using a substituent containing a carboxyl group or hydroxyl group for $R^3$ without reference to the number of addition mols of the EO mentioned above. As the (poly)alkylene glycol higher alkyl ether derivative composition that fits the increase of the HLB, ether carboxylic acid (salt) derivative, partially etherified derivatives with polyhydric alohol, and partially esterified derivatives with polycarboxylic acid may be cited.

For the sake of lowering the HLB (decreasing the proportion of hydrophilicity), it suffices to increase the content of the alkylene oxide such as oxypropylene group (PO) or oxypbutylene group (BO) in the total amount of the oxyalkylene group [AO in the general formula (1)] of the (poly)alkylene glycal higher alkyl ether derivative composition besides decreasing the number of addition moles of the oxyethylene group (EO) in the total amount of the oxyalkylene group [AO in the general formula (1)] of the (poly)alkylene glycol higher alkyl ether derivative composition. The HLB can be lowered by selecting as the (poly)alkylene glycol higher alkyl ether derivative composition such a composition that has a large number of carbon atoms for $R^3$ and contains no such hydrophilic substituent as hydroxyl group or carboxyl group. As concrete examples of the (poly)alkylene glycol higher alkyl ether derivative composition that fits this decrease of HLB, ester derivatives with a monohydric alcohol of 4–60 carbon atoms, preferably 8–30 carbon atoms and ester derivatives with a monovalent carboxyl acid may be cited.

When the (poly)alkylene glycol higher alkyl ether derivative composition of this invention is used as a dermatological medicine for external use, it can be used particularly advantageously in a configuration which comprises 30–90 mol. % of the (B1) derivative having a methyl group for $R^1$ and 70–10 mol. % of the (B2) derivative having an alkyl group of not less than two carbon atoms for $R^1$, preferably 40–80 mol. % of the (B1) derivative and 60–20 mol. % of the (B2) derivative, in the general formula (1). The (poly)alkylene glycol higher alkyl ether derivative composition which comprises the (B1) derivative and the (B2) derivative in a ratio in the aforementioned range manifests a particularly excellent base oil or a surfactant.

By using the (poly)alkylene glycol higher alkyl ether derivative composition with the HLB (hydrophilicity lipophilicity ratio) controlled as described above, the dermatological medicine for external use to be obtained excels in low stimulating property, low odor, emulsifying property, dispersing property, and solubilizing property.

As concrete examples of the dermatological medicine for external use contemplated by this invention, toilet soap, cleansing cream, cleansing lotion, rinse, skin cream, skin milk, emolient cream, cosmetic lotion, perfume, eau de Cologne, toilet oil, hair toilet articles, pomade, tiqueur, hair cream, hair dye, pasty perfume, powder, pack, shaving cream, shaving lotion, sunburn oil, suntan cream, sunburn lotion, suntan lotion, sunburn cream, suntan cream, foundation, massage cream, lip stick, lip cream, rouge, eye makeup, mascara, eyebrow pencil, nail enamel, enamel remover, hair dye, bath cosmetic article, tooth paste, deodorant, hair tonic and hair grower, cartilage, and poultice and medicated lip cream may be cited.

The dermatological medicine for external use contemplated by this invention, when necessary, may incorporate therein various known additives such as oily components other than the (poly)alkylene glycol higher alkyl ether derivative composition mentioned above, phospholipids, alcohols, water-soluble macromolecular compounds, moisture retaining agents, thickeners, geling agents, saccharides, surfactants-emulsifiers-solubilizers dispersants other than the (poly)alkylene glycol higher alkyl ether derivative composition mentioned above, ultraviolet absorbents, antiseptic agents, fuming agents, antioxidants, whitening agents, fluorescent materials, organic pigments, inorganic pigments, organic powders, inorganic powders, pigments, perfumes, sequestering agents, pH adjusting agents, binders, extenders, vitamins, amino acids, hormones, peptides, physiologically active extractants, nutrient components, bactericides, cuticle ameliorating agents, cuticle solving agents, antibiotics, skin permeation promoters, blood circulation promotors, antiphlogistics, cytotonic agents, anti-inflammatory agents, analgesic agents, skin softeners, skin palliative agents, would healing agents, and metabolism promoters in suitable amounts. These additives may be used either singly or in the form of a combination of two or more members.

The dermatological medicine for external use contemplated by this invention, when necessary, may be used in combination with known base oils besides the (poly)alkylene glycol higher alkyl ether derivative composition. For such known base oils, various vegetable oils, animal oils, mineral oils and synthetic oils may be used. As concrete examples of the base oil, oily fats such as olive oil, leaf oil, mink oil, and tree wax; waxes such as honey wax and candellila wax; mineral oils such as liquid paraffin, microcrystalline wax, and vaselin; fatty acids such as stearic acid and oleic acid; higher alcohols such as cetyl alcohol, 2-octyl dodecanol, and isostearyl alcohol; esters such as isopropyl myristate, lanolin derivatives such as isopropyl fatty acid lanolin and lanolin alcohol; starch fatty esters; silicon compounds such as methylphenyl polysiloxane, dimethyl polysilixane; and fluorine type oily agents such as perf luoropolyether may be cited. These base oils may be used either singly or in the form of a combination of two or more members.

The dermatological medicine for external use contemplated by this invention, when necessary, may be used in combination with known surfactants other than the (poly)alkylene glycol higher alkyl ether derivative composition. As concrete examples of the known surfactants, nonionic surfactants such as sorbitan fatty acid esters, polyoxyethylene sorbitan fatty acid esters, polyglycerin fatty acid esters, glycerin fatty acid esters, polyoxyethylenefattyacidesters, andpolyoxyethylenealkyl ethers and polyoxyethylene alkyl aryl ethers other than those of this invention; anionic surfactants such as higher fatty acid salts, ether carboxylic acid salts, and higher alkylsulfonic acid salt; and cationic surfactants such as alkyl quaternary ammonium salts, polyamines, and alkylamine salts may be cited. These surfactants may be used either singly or in the form of a combination of two or more members.

Now, this invention will be described more specifically below by reference to working examples.

(Production of (poly)alkylene glycol monoalkyl ether)

REFERENCIAL EXAMPLE 1

A dodecene isomer mixture consisting of 25 mol. % of 1-dodecene and 75 mol. % of inner dodecene was obtained by causing 1-dodecene to react with 5 wt. % of a BEA type zeolite (made by PQ Corp. and sold under the trademark designation of "Valfor CP811 BL-25") in a liquid phase at 150° C. for 10 hours.

In a glass reaction vessel, 3000 ml in inner volume, provided with a stirrer and a reflux condenser, 810 g of the dodecene isomer mixture, 900 g of monoethylene glycol, and 100 g of a BEA type zeolite (made by PQ Corp. and sold under the trademark designation of "Valfor CP811 BL-25") were left reacting in an atmosphere of nitrogen at 150° C. for three hours. After the reaction, the reaction solution was cooled to room temperature and allowed to undergo phase separation. The dodecene phase forming the upper layer in consequence of the phase separation was separated and distilled. After expelling the unaltered dodecene by evaporation, 155 g of secondary dodecanol monoethoxylate having boiling points in the range of 129–131° C. under a reduced pressure of 2 mmHg was obtained.

This secondary dodecanol monoethoxylate was found by NMR analysis to comprise 71 mol. % of an ethoxylate having a methyl group for $R^1$ and the balance of an ethoxylate having not lower than ethyl group for $R^1$ in the aforementioned general formula (2).

REFERENTIAL EXAMPLE 2

In a glass reaction vessel, 3000 ml in inner volume, provided with a stirrer and a reflux condenser, 810 g of the dodecene (a mixture obtained in the same manner as in Referential Example 1 and consisting of 25 mol. % of a-dodecene and 75 mol. % of inner dodecene), 1000 g of triethylene glycol, and 100 g of a BEA type zeolite (made by PQ Corp. and sold under the trademark designation of "Valfor CP811 BL-25") were left reacting in an atmosphere of nitrogen at 150° C. for three hours. After the reaction, the reaction solution was cooled to room temperature and allowed to undergo phase separation. The dodecene phase forming the upper layer in consequence of the phase separation was separated and distilled. After expelling the unaltered dodecene by evaporation, 135 g of secondary dodecanol triethoxylate having boiling points in the range of 205–210° C. under a reduced pressure of 2 mmHg was obtained.

This secondary dodecanol triethoxylate was found by NMR analysis to comprise 65 mol. % of an ethoxylate having a methyl group for $R^1$ and the balance of an ethoxylate having not lower than ethyl group for $R^1$ in the aforementioned general formula (2).

REFERENTIAL EXAMPLE 3

In a stainless steel autoclave, after having the entrapped air displaced with nitrogen, 155 g (0.67 mol) of secondary dodecanol monoethoxylate of Referential Example 1 and 0.2 g of sodium hydroxide were heated to 110° C. and dehydrated under 50 mmHg for one hour. Then, the mixture was heated to 150° C., made to introduce 217 g (4.93 mols) of ethylene oxide therein over a period of three hours, then retained further at 150° C. for one hour, then cooled, and purged of the inner gas to obtain secondary dodecanol polyethoxylate as a reaction product. The number of addition mols of ethylene oxide in the secondary dodecanol polyethoxylate was found to be 8.3 mols on average (the ethylene glycol added in Referential Example 1 included in the addition mols of ethylene oxide, similarly applicable hereinafter).

REFERENTIAL EXAMPLE 4

In a glass reaction vessel, 5000 ml in inner volume, provided with a stirrer and a reflux condenser, 1680 g of 1-dodecene, 1860 g of monoethylene glycol, and 206 g of a BEA type zeolite (made by PQ Corp. and sold under the trademark designation of "Valfor CP811 BL-25") were left reacting in an atmosphere of nitrogen at 150° C. for 10 hours. After the reaction, the reaction solution was cooled to room temperature and allowed to undergo phase separation. The dodecene phase forming the upper layer in consequence of the phase separation was separated and distilled batchwise. After expelling the unaltered isomerized dodecene (the 1-dodecene content of the dodecene was found by the analysis of NMR to be 7 mol. %) by evaporation, 276 g of a fraction having boiling points in the range of 135–137° C. under a reduced pressure of 3 mmHg. This fraction was identified as secondary dodecanol monoethoxylate. It was found by NMR analysis to comprise 70 mol. % of ethoxylate having methyl group for $R^1$ and the balance of ethoxylate having not lower than ethyl group for $R^1$ in the aforementioned general formula (2).

REFERENTIAL EXAMPLE 5

A reaction was performed by following the procedure of Referential Example 4 while using 1960 g of 1-tetradecene in the place of 1-dodecene. After the reaction, the reaction solution was cooled to room temperature and allowed to undergo phase separation. The tetradecene phase forming the upper layer in consequence of the phase separation was separated and distilled batchwise. After expelling the unaltered isomerized tetradecene (the 1-tetradecene content of the tetradecene was found by the analysis of NMR to be 7 mol. %) by evaporation, 306 g of a fraction having boiling points in the range of 155–157° C. under reduced pressure of 3 mmHg was recovered. This fraction was identified to be secondary tetradecanol monoethoxylate. By the NMR analysis, it was found to comprise 67 mol. % of ethoxylate having a methyl group for $R^1$ and the balance of ethoxylate having not lower than ethyl group for $R^1$ in the aforementioned general formula (2).

REFERENTIAL EXAMPLE 6

A reaction was performed by following the procedure of Referential Example 4 while using 2240 g of 1-hexadecene in the place of 1-dodecene. After the reaction, the reaction solution was cooled to room temperature and allowed to undergo phase separation. The hexadecene phase forming the upper layer in consequence of the phase separation was separated and distilled batchwise. The unaltered isomerized hexadecene (the content of 1-hexadecene in the hexadecene was found by the NMR analysis to be 6 mol. %) was expelled by evaporation to recover 314 g of a fraction having boiling points in the range of 170–172° C. under a reduced pressure of 2 mmHg. This fraction was identified to be secondary hexadecanol monoethoxylate. It was found by the NMR analysis to comprise 68 mol. % of ethoxylate having a methyl group for $R^1$ and the balance of ethoxylate having not lower than ethyl group for $R^1$ in the aforementioned general formula (2).

REFERENTIAL EXAMPLE 7

In a glass reaction vessel, 5000 ml in inner volume, provided with a stirrer and a reflux condenser, 1680 g of 1-dodecene, 2280 g of monopropylene glycol, and 254 g of a BEA type zeolite (made by PQ Corp. and sold under the trademark designation of "Valfor CP811 E-22") were left reacting in an atmosphere of nitrogen at 150° C. for 10 hours. After the reaction, the reaction solution was cooled to room temperature and allowed to undergo phase separation. The dodecene phase forming the upper layer in consequence of the phase separation was separated and distilled batchwise. After expelling the unaltered isomerized dodecene (the 1-dodecene content of the dodecene was found by the analysis of NMR to be 7 mol. %) by evaporation, 240 g of a fraction having boiling points in the range of 140–142° C. under a reduced pressure of 3 mmHg. This fraction was identified as secondary dodecanol monopropoxylate. It was found by NMR analysis to comprise 80 mol. % of ethoxylate having methyl group for $R^1$ and the balance of ethoxylate having not lower than ethyl group for R in the aforementioned general formula (2).

REFERENTIAL EXAMPLE 8

In a stirring type stainless steel autoclave, 500 ml in inner volume, after having the entrapped air displaced with nitrogen, 50.0 g of secondary dodecanol monoethoxylate of Referential Example 4 and 0.15 g of potassium hydroxide were heated to 110° C. and dehydrated under 50 mmHg for one hour. Then, the mixture was heated to 150° C., made to introduce 57.4 g of ethylene oxide therein over a period of three hours, and then retained further at 150° C. for one hour. After the reaction, the reaction solution was cooled and purged of the inner gas to obtain secondary dodecanol polyethoxylate. The number of addition mols of ethylene oxide in the polyethoxylate was found to be 7 mols on average (the ethylene glycol added in Referential Example 4 included in the addition mols of ethylene oxide, similarly applicable hereinafter).

REFERENTIAL EXAMPLE 9

By following the procedure of Referential Example 8, a secondary tetradecanol polyethoxylate having 59.7 g of ethylene oxide added to 50.0 g of the secondary tetradecanol monoethoxylate of Referential Example 5 was obtained. The number of addition mols of ethylene oxie in the polyethoxylate was found to be 8 mols on average.

REFERENTIAL EXAMPLE 10

By following the procedure of Referential Example 8, a secondary hexadecanol polyethoxylate having 15.4 g of ethylene oxide added to 50.0 g of the secondary hexadecanol monoethoxylate of Referential Example 6 was obtained. The number of addition mols of ethylene oxie in the polyetlhoxylate was found to be 3 mols on average.

REFERENTIAL EXAMPLE 11

In a stirring type stainless steel autoclave, 500 ml in inner volume, after having the entrapped air displaced with nitrogen, 50.0 g of secondary dodecanol monoethoxylate of Referential Example 4 and 0.15 g of potassium hydroxide were heated to 110° C. and dehydrated under 50 mmHg for one hour. Then, the mixture was heated to 150° C., made to introduce 38.2 g of ethylene oxide therein over a period of three hours, and then retained further at 150° C. for one hour. After the reaction, the reaction solution was cooled to 120° C. and made to introduce 126.1 g of propylene oxide therein over a period of three hours. The reaction solution was further retained for one hour. After the reaction, the reaction solution was cooled and purged of the inner gas to obtain secondary dodecanol polyalkoxylate. The number of addition mols of ethylene oxide in the polyalkoxylate was found to be 5 mols on average and the number of addition mols of propylene oxide to be 10 mol on average.

REFERENTIAL EXAMPLE 12

By following the procedure of Referential Example 11, a secondary hexadecanol polyalkoxylate having 30.8 g of ethylene oxide added at 150° C., 101.4 g of propylene oxide at 120° C., and 38.4 g of ethylene oxide at 150° C. to 50.0 g of the secondary hexadecanol monoethoxylate of Referential Example 6 was obtained. This polyalkoxylate was identified to be a block polymer comprising 5 mols of ethylene oxide, 10 mols of propylene oxide, and 5 mols of ethylene oxide in terms of the number of addition mols of alkylene oxide on average.

REFERENTIAL EXAMPLE 13

By following the procedure of Referential Example 11, a polypropoxylate having 106.9 g of propylene oxide added at 120° C. to 50.0 g of the secondary dodecanol monopropoxylate of Referential Example 7 was obtained. The number of addition mols of propylene oxide in the polypropoxylate was found to be 10 mols. on average.

REFERENTIAL EXAMPLE 14

By following the procedure of Referential Example 11, a polyalkoxylate having 106.9 g of propylene oxide added at 120° C. and then 45.1 g of ethylene oxide at 150° C. to 50.0 g of the secondary dodecanol monopropoxylate of Referential Example 7. In this polyalkoxylate, the number of addition mols of propylene oxide was found to be 10 mols on average and the number of addition mols of ethylene oxide to be 5 mols on average.

(Production of (poly)alkylene glycol dialkyl ether)

Example 1

From the distillation bottom remaining after the recovery of the secondary dodecanol monoethoxylate of Referential Example 4, 165 g of a fraction having boiling temperatures in the range of 218–232° C. was recovered under a reduced pressure of 2 mmHg. This fraction was identified to be di-secondary dodecyl ether of monoethylene glycol resulting from further addition of dodecene to the secondary dodecyl alcohol monoethoxylate formed during the reaction of Referential Example 4.

The infrared absorption spectrum of the substance mentioned above is shown in FIG. 1. The diagram shows no discernible sign of the absorption originating in the OH group near 3500 cm$^{-1}$. By the GLC analysis of the di-secondary dodecyl ether of monoethylene glycol, the proportion of the methyl group for $R^1$ in at least either of the secondary dodecyl groups was found to be 62 mol. %.

Example 2

In an autoclave provided with a stirrer, after having the gas phase thereof displaced with nitrogen gas, 318 g (1.0 mol) of the secondary dodecanol triethoxylate of Referential Example 2 and 80 g (2.0 mols) of sodium hydroxide in the form of flakes were left reacting at 60° C. Then, 56 g (1.1 mols) of methyl chloride was introduced into the autoclave, with the contents thereof kept stirred, over a period of three hours. After the introduction, the reactants in the autoclave were further heated to 90° C. and left reacting for one hour. After the reaction, the reaction solution was extracted. When the organic layer was separated and analyzed, the yield of the secondary dodecanol triethoxylate methyl ether was found to be 95 mol. %. The hydroxyl value was found to be 4.5 mg KOH/g and the presence of a terminal methyl group was confirmed by the NMR analysis (3.2 ppm, singlet).

Example 3

In an autoclave provided with a stirrer, after the gas phase thereof displaced with nitrogen gas, 551 g (1.0 mol) of the secondary dodecanol polyethoxylate of Referential Example 3 and 80 g (2.0 mols) of sodium hydroxide in the form of flakes were left reacting at 60° C. Then, 56 g (1.1 mols) of methyl chloride was introduced into the autoclave, with the contents of the autoclave kept stirred, over a period of three hours. After the introduction, the reactants in the autoclave were further heated to 90° C. and left reacting for one hour. After the reaction, the reaction solution was extracted from the autoclave. When the organic layer was separated and analyzed, the yield of the secondary dodecanol polyethoxylate methyl ether was 95 mol. %. The hydroxyl value was found to be 4.0 mgKOH/g and the presence of a terminal methyl group was confirmed by the NMR analysis (3.2 ppm, singlet).

(Production of ether carboxylic acid (salt))

Example 4

In a glass reaction vessel provided with a stirrer, 551 g (1.0 mol) of the secondary dodecanol polyethoxylate of Referential Example 3 and 99.2 g (1.05 mols) of monochloroacetic acid were homogeneously dissolved and 175 g (2.1 mols) of an aqueous 48% sodium hydroxide solution was added dropwise to the solution over a period of two hours. In this while, the reactants were kept under the conditions of 60° C. and 20 mmHg to expel from the system the water contained in the aqueous sodium hydroxide solution and the water formed by the reaction. After the dropwise addition, the reactants were kept under the same conditions for one hour to obtain a white viscous liquid resembling a slurry. This reaction product and ethanol added thereto in an equal amount were stirred to form a homogenous slurry. The slurry was filtered to remove by-produced sodium chloride and further subjected to vacuum concentration to expel ethanol. The composition consequently obtained was found to comprise 95 wt. % of ether carboxylic acid salt and 5 wt. % of unaltered ethoxylate. It assumed a state of paste at normal room temperature. The purity was determined by means of liquid chromatography using a column packed with anion-cation exchange resins.

Figure 2:
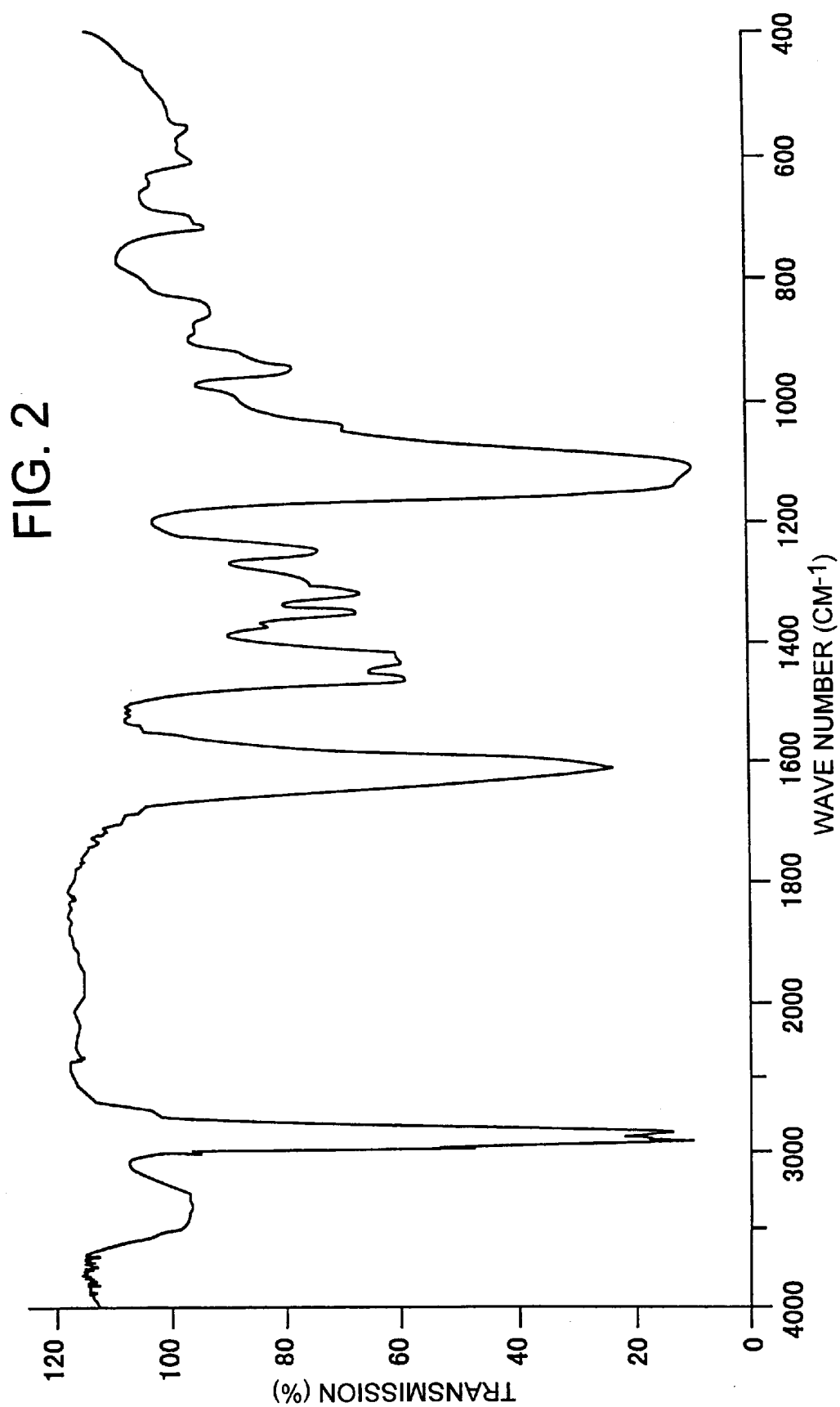
FIG. 2 is a diagram showing the infrared absorption spectrum of the compound obtained in Example 4.

The infrared absorption spectrum of the pasty substance mentioned above is shown in FIG. 2. The diagram shows discernible peaks of carboxylic acid salt near 1610 cm$^{-1}$ and 1420 cm$^{-1}$. The diagram shows a slightly discernible absorption originating in the OH group near 3500 cm$^{-1}$.

Example 5

In a glass reaction vessel provided with a stirrer, 318 g (1.0 mol) of the secondary dodecanol triethoxylate of Referential Example 2 and 99.2 g (1.05 mols) of monochloroacetic acid were homogeneously dissoved and then 175 g (2.1 mols) of an aqueous 48% sodium hydroxide solution was added dropwise to the resultant solution over a period of two hours. In this while, the reactants were kept under the conditions of 60° C. and 20 mmHg to expel from the system the water contained in the aqueous sodium hydroxide solution and the water formed by the reaction. After the dropwise addition, the reactants were further kept under the same conditions for one hour to obtain a white viscous liquid resembling a slurry. The reaction product and ethanol added thereto in an equal amount were stirred to produce a homogeneous slurry. The slurry was filtered to remove by-produced sodium chloride and further subjected to vacuum distillation to expel ethanol. The composition consequently obtained was found to comprise 96 wt. % of ether carboxylic acid salt and 4 wt. % of unaltered alkoxylate and it assumed a state of paste at normal room temperature. The purity was determined by means of liquid chromatography using a column packed with anion-cation exchange resins.

(Production of carboxylic ester)

Example 6

In a glass reaction vessel provided with a reflux condenser fitted with a draining pipe, a thermometer, a nitrogen blow pipe, and a stirrer, 551 g (1.0 mol) of the secondary dodecanol polyethoxylate of Referential Example 3, 90 g (1.5 mols) of acetic acid, 5 g of paratoluenesulfonic acid, and 500 g of toluene were heated as swept meanwhile with nitrogen and then left reacting for five hours, with the water formed by the reaction extracted via the draining pipe at the reflux temperature. After the reaction, the reaction solution was made to add an aqueous sodium carbonate solution to extract the catalyst and the excess acetic acid into the water layer, separate the oil layer, remove the toluene under vacuum distillation, and obtain the reaction product. When the product was analyzed, the yield of acetic ester was found to be 95 mol. % and the hydroxyl value to be 4.0 mg KOH/g.

Figure 3:
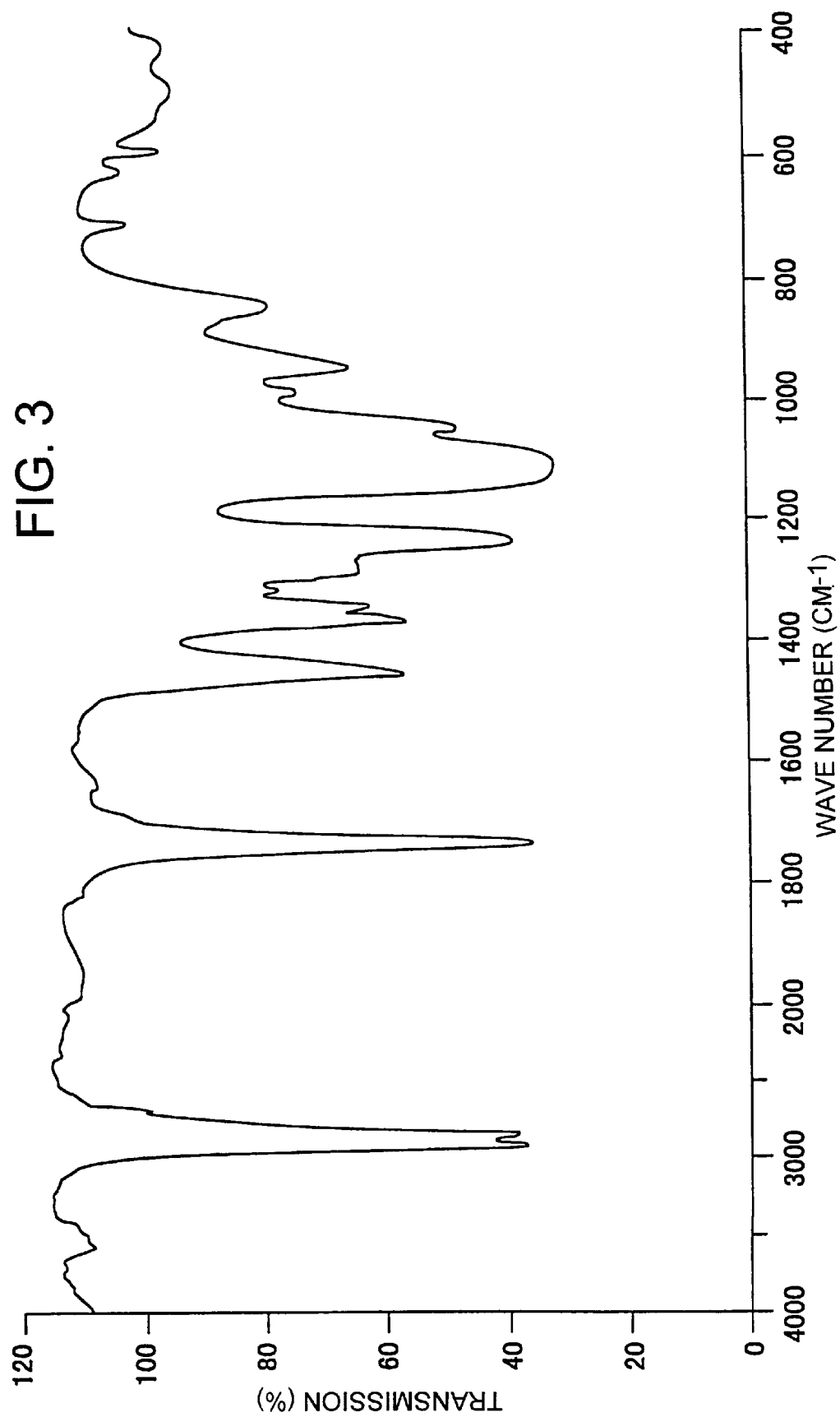
FIG. 3 is a diagram showing the infrared absorption spectrum of the compound obtained in Example 6.

The infrared absorption spectrum of the substance mentioned above is shown in FIG. 3. The diagram shows discernible absorption of an ester bond near 1740 cm$^{-1}$. It shows virtually no discernible absorption of OH group or carboxylic acid.

Example 7

In a glass reaction vessel provided with a reflux condenser fitted with a draining pipe, a thermometer, a nitrogen blow pipe, and a stirrer, 230 g (1.0 mol) of the secondary dodecanol monoethoxylate of Referential Example 4, 129 g (1.5 mols) of methacrylic acid, 5 g of paratoluenesulfonic acid, 0.2 g of hydroquinone monomethyl ether, and 200 g of toluene were heated as swept meanwhile with nitrogen and then left reacting for five hours, with the water formed by the reaction extracted via the draining pipe at the reflux temperature. After the reaction, the reaction solution was made to add an aqueous sodium carbonate solution to extract the catalyst and the excess methacrylic acid into the water layer, separate the oil layer, remove the toluene under vacuum distillation, and obtain the reaction product. When the product was analyzed, the yield of methacrylic ester was found to be 96 mol. %.

Figure 4:
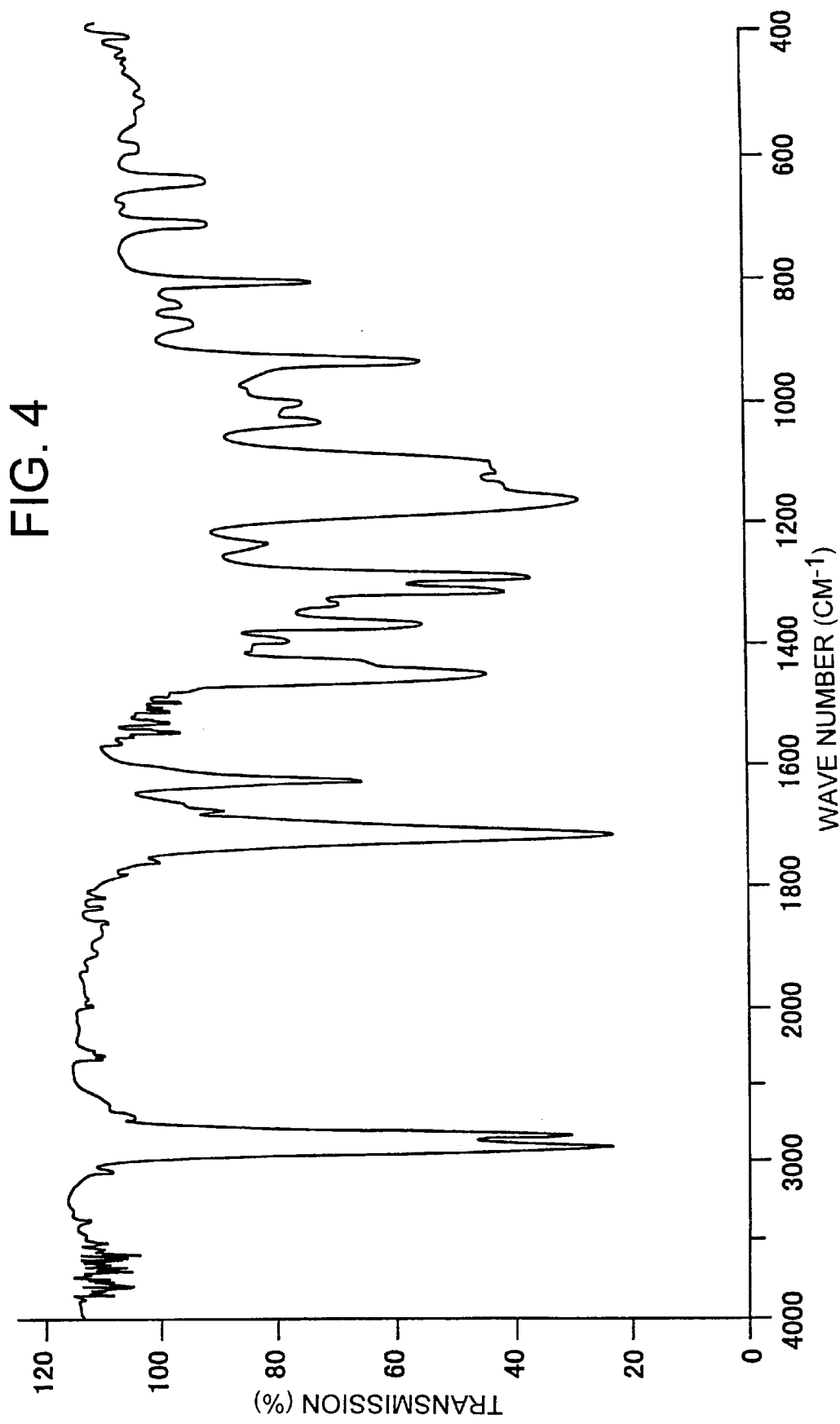
FIG. 4 is a diagram showing the infrared absorption spectrum of the compound obtained in Example 7.

The infrared absorption spectrum of the substance mentioned above is shown in FIG. 4. The diagram shows discernible absorption of an ester bond near 1720 cm$^{-1}$. It shows virtually no discernible absorption of OH group or carboxylic acid.

Example 8

In a glass reaction vessel provided with a reflux condenser fitted with a draining pipe, a thermometer, a nitrogen blow pipe, and a stirrer, 318 g (1.0 mol) of the secondary dodecanol triethoxylate of Referential Example 2, 108 g (1.5 mols) of acrylic acid, 5 g of paratoluenesulfonic acid, 0.2 g of hydroquinone monomethyl ether, and 500 g of toluene were heated as swept meanwhile with nitrogen and then left reacting for five hours, with the water formed by the reaction extracted via the draining pipe at the reflux temperature. After the reaction, the reaction solution was made to add an aqueous sodium carbonate solution to extract the catalyst and the excess acrylic acid into the water layer, separate the oil layer, remove the toluene under vacuum distillation, and obtain the reaction product. When the product was analyzed, the yield of acrylic ester was found to be 97 mol. % and the hydroxyl value to be 3.8 mg KOH/g. By the infrared absorption analysis, discernible absorption of an ester bond was recognized near 1720 cm$^{-1}$ and virtually no discernible absorption of OH group or carboxylic acid was recognized.

Example 9

In a glass reaction vessel provided with a thermometer, a condenser, a dropping funnel, and a stirrer, 99 g (1.01 mols) of maleic anhydride and 1.7 g of sodium acetate were placed and, after having the inner gas displaced with nitrogen gas, heated to 70° C. The resultant mixture and 495 g (1.0 mol) of the secondary dodecanol polyethoxylate of Referential Example 8 introduced thereto through the dropping funnel over a period of one hour were left reacting for four hours. Subsequently, with the temperature elevated to 100° C., the reaction was continued for one hour. After the reaction, the reaction solution was cooled to obtain maleic half ester.

Figure 5:
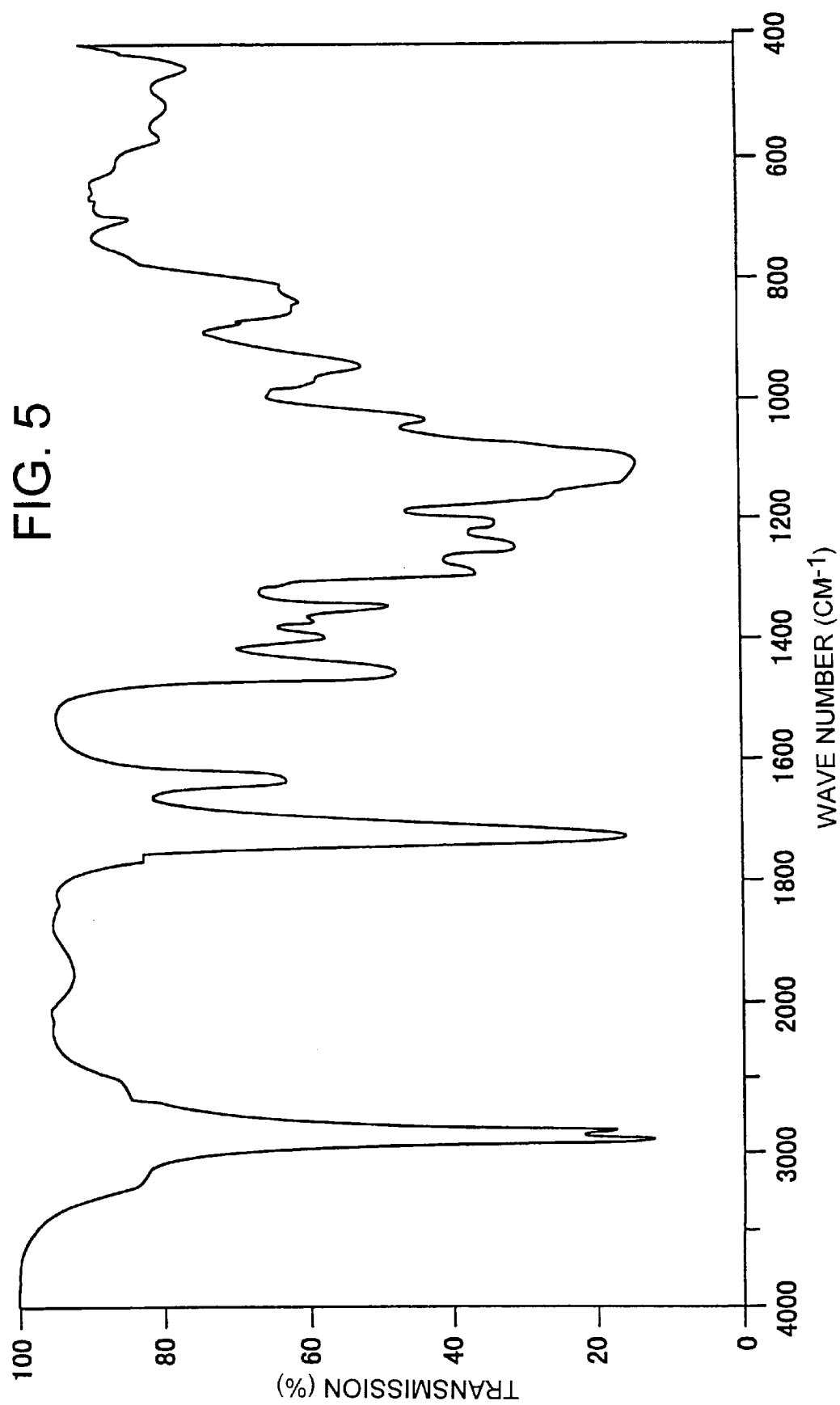
FIG. 5 is a diagram showing the infrared absorption spectrum of the compound obtained in Example 9.

The infrared absorption spectrum of the substance mentioned above is shown in FIG. 5. The diagram shows discernible absorption of an ester bond near 1730 cm$^{-1}$ and shows virtually no discernible absorption of OH group or acetic anhydride.

Example 10

In a glass reaction vessel provided with a thermometer, a condenser, a dropping funnel, a nitrogen introducing capillary tube, and a stirrer, 49.4 g (0.33 mol) of phthalic anhydride and 1.4 g of dibutyl tin dilaurate were placed and, after having the inner gas displaced with nitrogen, heated to 150° C. To the resultant mixture in the reaction vessel, 230 g (1.0 mol) of the secondary dodecanol monoethoxylate of Referential Example 4 was added through the dropping funnel over a period of two hours. After the addition, the temperature of the mixture was elevated to 180° C. and the reaction was continued for three hours, with the water formed by the reaction expelled by nitrogen bubbling. Under the conditions of the same temperature and a reduced pressure of 10 mmHg, the reaction system was bubbled with nitrogen gas to expel the unaltered secondary dodecanol monoethoxylate. Then, the reaction solution was cooled to obtain phthalic diester.

Figure 6:
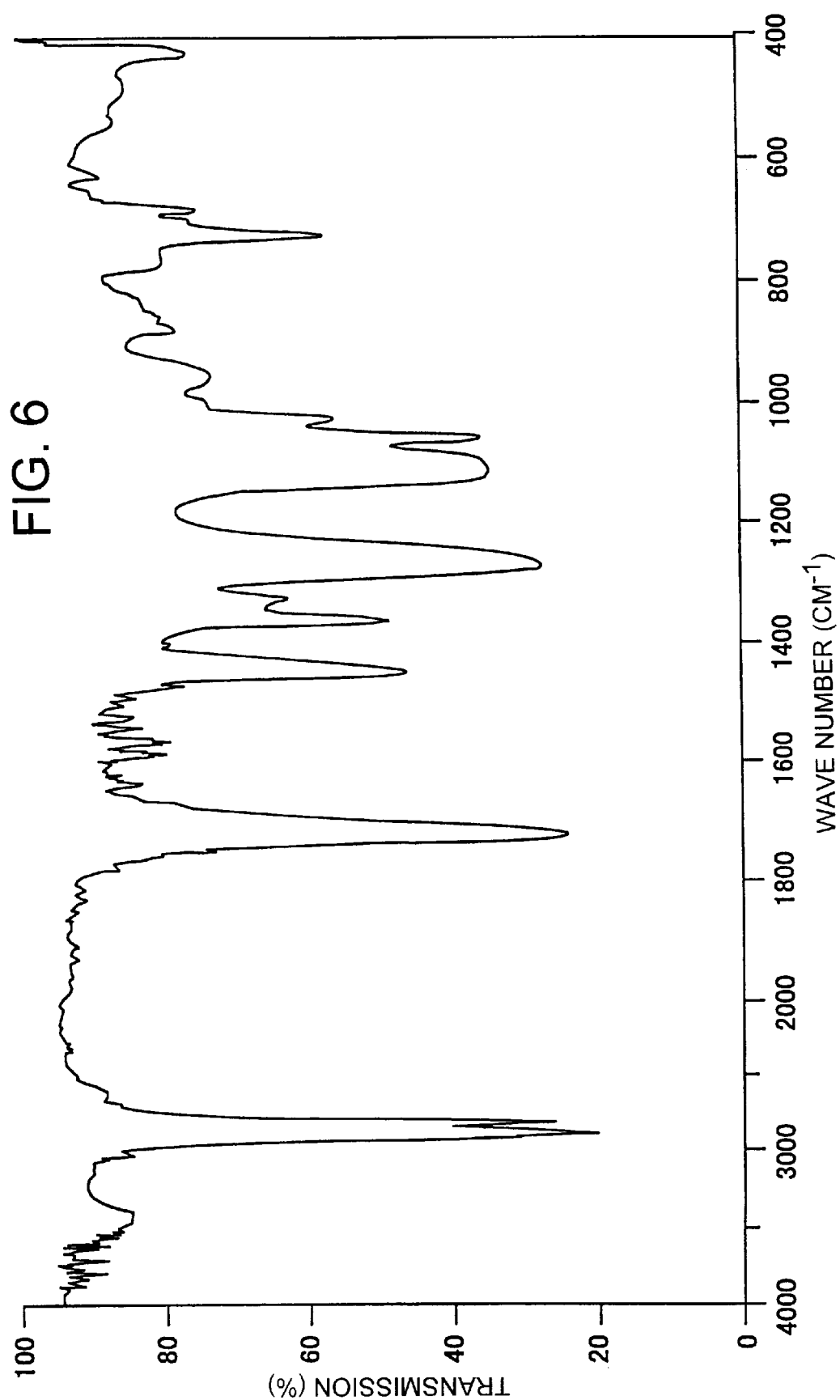
FIG. 6 is a diagram showing the infrared absorption spectrum of the compound obtained in Example 10.

The infrared absorption spectrum of the substance mentioned above is shown in FIG. 6. The diagram shows a discernible absorption of an ester bond near 1730 cm$^{-1}$ and shows virtually no discernible absorption of OH group or acid anhydride.

Example 11

In a glass reaction vessel provided with a thermometer, a concenser, a nitrogen introducing capillary tube, and a stirrer, 230 g (1.0 mol) of the secondary dodecanol monoethoxylate of Referential Example 4, 259 g (0.91 mol) of stearic acid, and 2.4 g of dibutyl tin dilaurate were placed, heated to 180° C. and bubbled meanwhile with nitrogen gas, and then left reacting for three hours. Under the conditions of the same temperature and a reduced pressure of 10 mmHg, the reaction system was bubbled with nitrogen gas to expel the unaltered secondary dodecanol monoethoxylate. Then, the reaction solution was cooled to obtain stearic ester.

Figure 7:
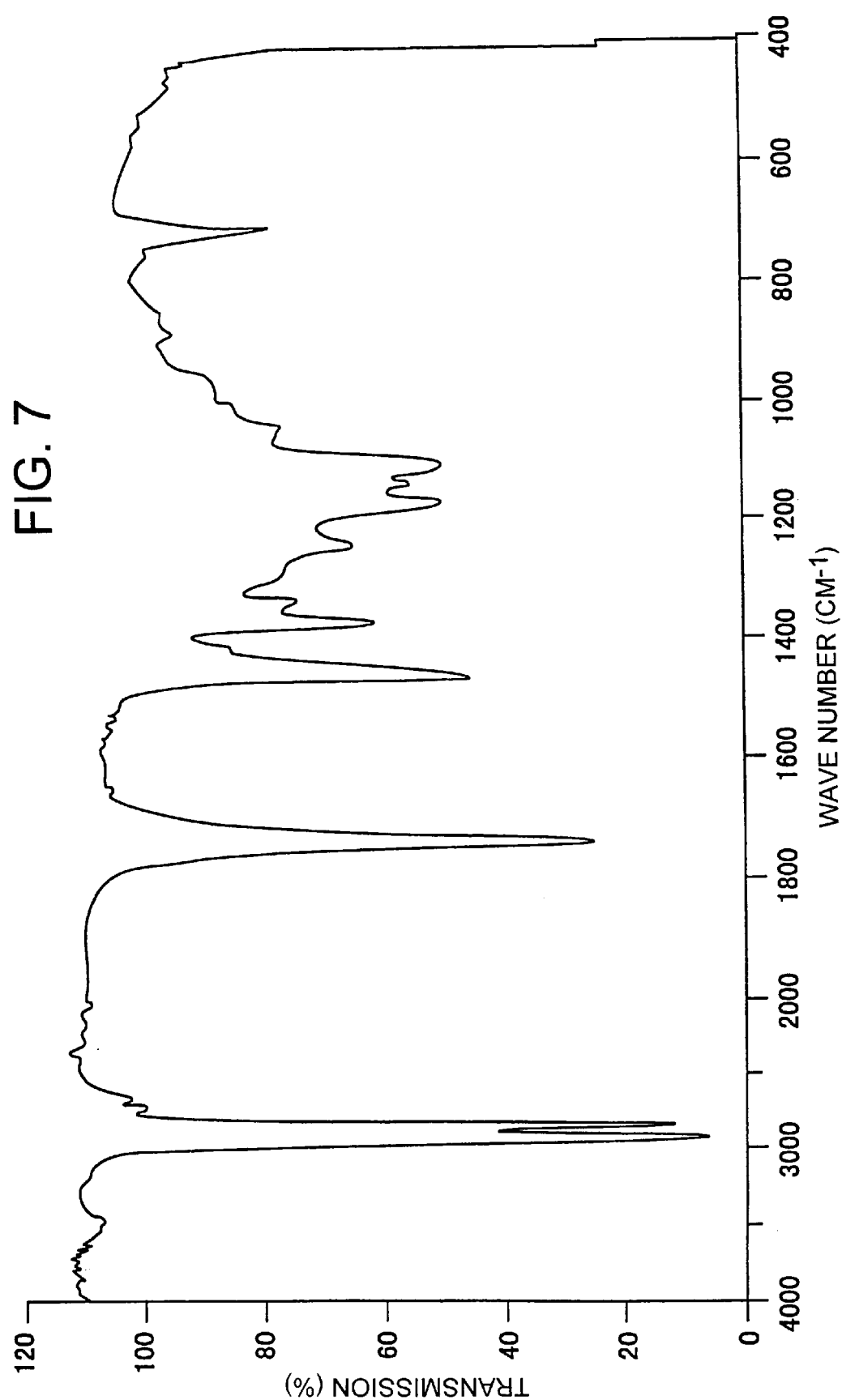
FIG. 7 is a diagram showing the infrared absorption spectrum of the compound obtained in Example 11.

The infared absorption spectrum of the substance mentioned above is shown in FIG. 7. The diagram shows a discernible absorption of an ester bond near 1740 cm$^{-1}$ and shows virtually no discernible absorptionof OH group or carboxylic acid.

Example 12

Stearic ester was obtained by causing 244 g (1.0 mol) of the secondary dodecanol monopropoxylate of Referential Example 7, 259 g (0.91 mol) of stearic acid, and 2.5 g of dibutyl tin dilaurate to react by following the procedure of Example 11.

Example 13

In a glass reaction vessel provided with a thermometer, a condenser, a nitrogen introducing capillary tube, and a stirrer, 247 g (0.5 mol) of the secondary dodecanol polyethoxylate of Referential Example 8, 129 g (0.45 mol) of stearic acid, and 1.9 g of dibutyl tin dilaurate were placed, heated to 180° C. and bubbled meanwhile with nitrogen gas, and then left reacting for three hours. Under the conditions of the same temperature and a reduced pressure of 10 mmHg, the reaction system was bubbled with nitrogen gas to expel the water formed by the reaction. Then, the reaction solution was cooled to obtain stearic ester.

Example 14

Stearic ester was obtained by causing 283 g (0.5 mol) of the secondary tetradecanol polyethoxylate of Referential Example 9, 129 g (0.45 mol) of stearic acid, and 2.1 g of dibutyl tin dilaurate to react in the same procedure as in Example 13.

Example 15

Stearic ester was obtained by causing 187 g (0.5 mol) of the secondary hexadecanol polyethoxylate of Referential Example 10, 129 g (0.45 mol) of stearic acid, and 1.6 g of dibutyl tin dilaurate in the same procedure as in Example 13.

Example 16

Stearic ester was obtained by causing 494 g (0.5 mol) of the secondary dodecanol polyalkoxylate of Referential Example 11, 129 g (0.45 mol) of stearic acid, and 3.1 g of dibutyl tin dilaurate to react in the same procedure as in Example 13.

Example 17

Stearic ester was obtained by causing 632 g (0.5 mol) of the secondary hexadedanol polyalkoxylate of Referential Example 12, 129 g (0.45 mol) of stearic acid, and 3.8 g of dibutyl tin dilaurate to react in the same procedure as in Example 13.

Example 18

Stearic ester was obtained by causing 384 g (0.5 mol) of the secondary dodecanol polypropoxylate of Referential Example 13, 129 g (0.45 mol) of stearic acid, and 2.6 g of dibutyl tin dilaurate to react in the same procedure as in Example 13.

Example 19

Stearic ester was obtained by causing 494 g (0.5 mol) of the secondary dodecanol polyalkoxylate of Referential Example 14, 129 g (0.45 mol) of stearic acid, and 3.1 g of dibutyl tin dilaurate to react in the same procedure as in Example 13.

Example 20

Hydroxystearic ester was obtained by causing 230 g (1.0 mol) of the secondary dodecanol monoethoxylate of Referential Example 4, 273 g (0.91 mol) of hydroxystearic acid (a reagent made by Wako Pure Chemical Industries, Ltd. and having a minimum purity of 70% and containing 10% of stearic acid), and 2.5 g of dibutyl tin dilaurate to react in the same procedure as in Example 11.

Figure 8:
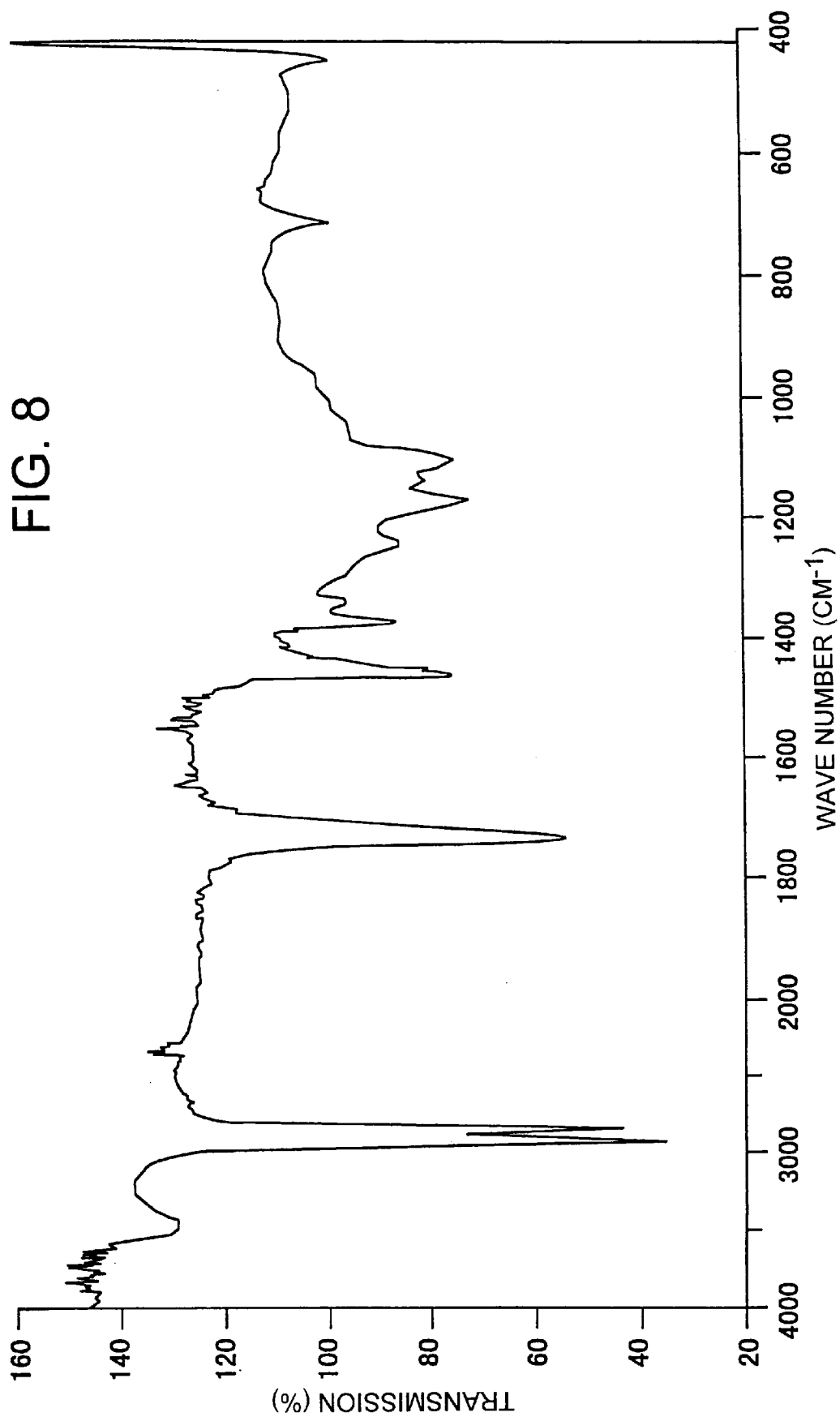
FIG. 8 is a diagram showing the infrared absorption spectrum of the compound obtained in Example 20.

The infrared absorption spectrum of the substance mentoioned above is shown in FIG. 8. The diagram shows discernible absorption of ester bond near 1740 cm$^{-1}$ and shows no discernible absoption of carboxylic acid.

Example 21

Isostearic ester was obtained by causing 286 g (1.0 mol) of the secondary hexadecanol monoethoxylate of Referential Example 6, 259 g (0.91 mol) of isostearic acid, and 2.7 g of dibutyl tin dilaurate to react in the same procedure as in Example 11.

Example 22

Hydroxystearic ester was obtained by causing 230 g (1.0 mol) of the secondary dodecanol monoethoxylate of Referential Example 4, 300 g (1.0 mol) of hydroxystearic acid (a reagent made by Wako Pure Chemical Industries, Ltd. and having a minimum purity of 70% and containing 10% of stearic acid), 2.7 g of dibutyl tin dilaurate to react in the same procedure as in Example 13. This reaction product and 600 g (2.0 mols) of hydrbxystearic acid and 1.6 g of sulfuric acid added thereto are heated together to 180° C. and bubbled meanwhile with nitrogen gas and then left reacting for three hours. Under the conditions of the same temperature and a reduced pressure of 10 mmHg, the system was bubbled with nitrogen for two hours to expel the water formed by the reaction. Subsequently, the reaction solution was cooled to obtain polyhydroxystearic ester.

Figure 9:
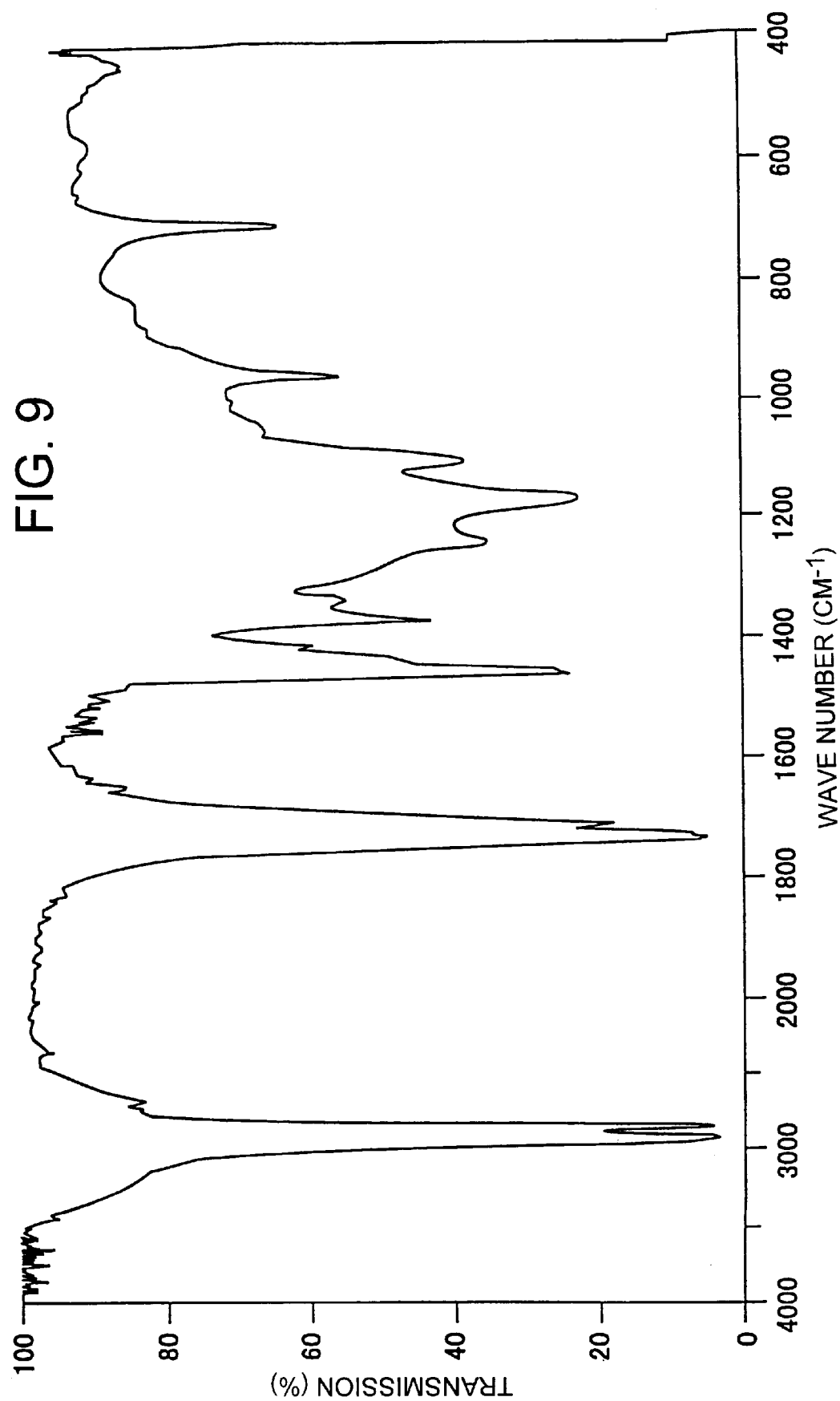
FIG. 9 is. a diagram showing the infrared absorption spectrum of the compound obtained in Example 22.

The infrared absorption spectrum of the substance mentioned above is shown in FIG. 9. The diagram shows a discernible absorption of ester bond near 1740 $cm^{-1}$ and, virtually no discernible absorption of OH group, and shows a slightly discernible absorption of carboxylic acid near 1710 $cm^{-1}$. It is suspected that the latter absorption was caused by stearic acid as an impurity.

Figure 10:
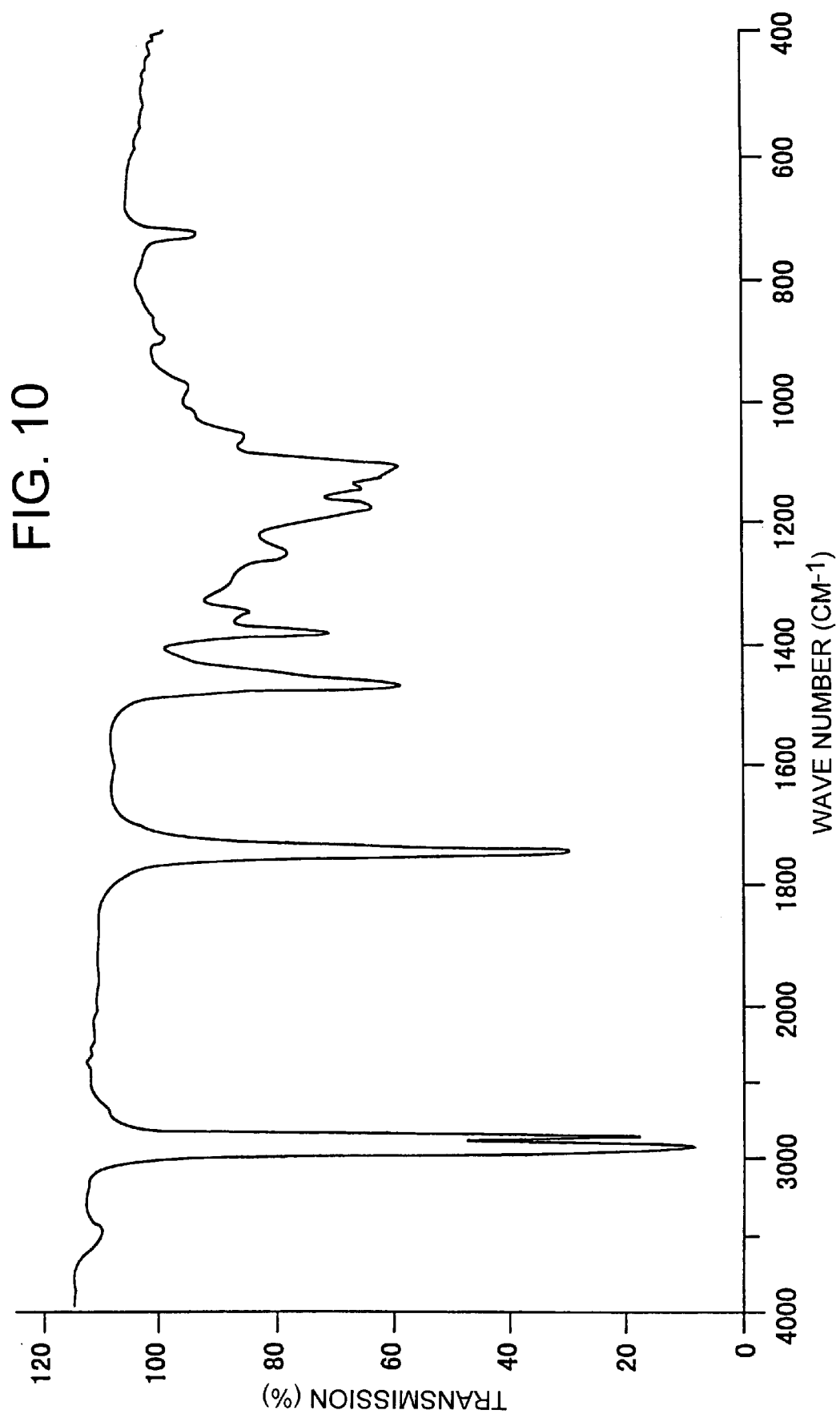
FIG. 10 is a diagram showing the infrared absorption spectrum of the compound obtained in Example 23.

The infrared absorption spectrum of the substance mentioned above is shown in FIG. 10. The diagram shows a discernible absorption of ester bond near 1740 $cm^{-1}$ and shows virtually no absorption of OH group.

(Rating as lubricating agent)

Examples 24–37

The compounds of Examples 1, 11–23 were rated for pour point, kinetic viscosity at 40° C., friction coefficient, and biodegradability.

The results are shown in Table 1.

Methods for rating

Pour point: In accordance with JIS K-2269, with necessary modifications

Kinetic viscosity: In accordance with JIS K-2283, with necessary modifications

Friction coefficient: Pendulum type friction tester

Biodegradability: In accordance with MITI method (25° C., 14 days), with necessary modifications [Controls 1 and 2]

PPG (polypropylene glycol, average molecular weight 1000) and mineral oil rated as comparative lubricating agents.

The results are shown in Table 1.

TABLE 1

| | Example | | | | | | | | | | | | | | Control | |
|---|---|---|---|---|---|---|---|---|---|---|---|---|---|---|---|---|
| | 24 | 25 | 26 | 27 | 28 | 29 | 30 | 31 | 32 | 33 | 34 | 35 | 36 | 37 | 1 | 2 |
| Compound (Example) | 1 | 11 | 12 | 13 | 14 | 15 | 16 | 17 | 18 | 19 | 20 | 21 | 22 | 23 | PPG | Mineral Oil |
| Number of carbon atoms of olefin | 12 | 12 | 12 | 12 | 14 | 16 | 12 | 16 | 12 | 12 | 12 | 16 | 12 | 16 | | |
| Addition alkylene glycol | EG | EG | PG | EG | EG | EG | EG | EG | PG | PG | EG | EG | EG | EG | | |
| Number of addition mols of EO | | | | 6 | 7 | 2 | 4 | 4 | | | | | | | | |
| Number of addition mols of PO | | | | | | | | 10 | 10 | 9 | 9 | | | | | |
| Number of addition mols of EO | | | | | | | | | 5 | | 5 | | | | | |
| Derivative | 12 | SA | SA | SA | SA | SA | SA | SA | SA | SA | HSA | ISA | PHSA | DIM | | |
| Pour point (° C.) | 0 | −10 | −35 | −5 | 0 | −30 | <−40 | <−40 | <−40 | <−40 | −15 | −40 | −40 | −40 | −40 | −10 |
| Kinetic viscosity ($mm^2/s$) | 20 | 19 | 18 | 48 | 56 | 32 | 55 | 72 | 48 | 65 | 63 | 18 | 150 | 280 | 45 | 84 |
| Friction coefficient | 0.16 | 0.15 | 0.14 | 0.15 | 0.15 | 0.14 | 0.14 | 0.14 | 0.14 | 0.14 | 0.15 | 0.14 | 0.14 | 0.15 | 0.17 | 0.30 |
| Biodegradability (%) | | 80 | | 85 | | | 70 | | | | 85 | | | | 24 | 15 |

EG — Ethylene glycol
HSA — Hydroxystearic ester
PG — Propylene glycol
ISA — Isostearic ester
12 — Dodecyl ether
PHSA — Polyhydroxystearic ester
SA — Stearic ester
DIM — Dimer ester

Example 23

A dimer diester was obtained by causing 286 g (1.0 mol) of the secondary hexadecanol monoethoxylate of Referential Example 6, 255 g (0.45 mol) of a dimer acid (made by Henkel and sold under the trademark of "Empol 1061"), and 2.1 g of dibutyl tin dilaurate to react in the same procedure of Example 11.

Examples 38–40

Aqueous 2% solutions of the compounds obtained in Examples 3, 5, and 6 were prepared and tested for friction coefficient by the use of a pendulum type friction tester. The results are shown in Table 2.

TABLE 2

| Example | 38 | 39 | 40 |
|---|---|---|---|
| Compound (Example) | 3 | 5 | 6 |
| Number of carbon atoms of olefin | 12 | 12 | 12 |
| Addition alkylene glycol | EG | TEG | EG |
| Number of addition mols of EO | 7.3 | | 7.3 |
| Number of addition mols of PO | | | |
| Number of addition mols of EO | | | |
| Derivative | Me | EC | Ac |
| Friction coefficient | 0.15 | 0.15 | 0.16 |

EG - Ethylene glycol
TEG - Triethylene glycol
Me - Methyl ether
EC - Ether carboxylic acid salt
Ac - Acetic ester (Production of cosmetic article (lip stick))

Example 41

A lip stick of the following formulation was produced. The following components were thoroughly heated and mixed at 70° C., cast in a mold, and suddenly cooled to obtain a lip stick. This lip stick produced satisfactory sensation of use.

The lip stick of this example was rated for stimulancy by a patch test (according to the Schwartz-Peck method with necessary modifications) performed on a panel of five members. After 48 hours of application to their lips, no positive test was reported by any of the panel members.

| | |
|---|---|
| Castor Oil | 25.0% |
| Lanolin | 10.0% |
| Cetyl 2-ethylhexanoate | 15.0% |
| Compound of Example 1 | 15.0% |
| Candelilla wax | 10.0% |
| Solid paraffin | 9.0% |
| Carnauba wax | 5.0% |
| Honey wax | 5.0% |
| Titanium dioxide | 5.0% |
| Coloring matter | 1.0% |

(Production of cosmetic material (soft cosmetic liquid))

Example 42

A soft cosmetic liquid of the following formulation was produced. The following components were thoroughly mixed at room temperature to obtain the cosmetic liquid. The soft cosmetic liquid produced a fully satisfactory sensation of use.

| | |
|---|---|
| Glycerin | 5.0% |
| Propylene glycol | 4.0% |
| Compound of Example 2 | 0.5% |
| Polyoxyethylene (20) sorbitan monolauryl ether | 2.0% |
| Ethanol | 10.0% |
| Perfume | 0.1% |
| Antiseptic-antioxidant agent | Suitable amount |
| Purified water | 78.9% |

(Production of cosmetic material (W/O massage cream))

Example 43

A massage cream of the following formulation was produced. A mixture of purified water with soap powder and a mixture of the remaining components were melted independently by being heated to 70° C. and the melts were mixed and homogeneously emulsified by a homomixer. The emulsion was cooled to obtain the massage cream. This massage cream produced a fully satisfactory sensation of use.

| | |
|---|---|
| Paraffin | 4.0% |
| Microcrystailine wax | 6.0% |
| Honey wax | 6.0% |
| Vaseline | 14.0% |
| Liquid paraffin | 42.5% |
| Sorbitan sesquioleate | 3.7% |
| Compound of Example 4 | 0.8% |
| Perfume | 0.5% |
| Antiseptic-antioxidant | Suitable amount |
| Soap powder | 0.3% |
| Purified water | 22.2% |

(Production of cosmetic material (emolient cream))

Example 44

An emolient cream of the following formulation was produced. The compound of Example 11 was purified by being first washed with water and then treated with activated clay. A mixture of purified water with propylene glycol and a mixture of the remaining components were heated independently to 70° C. and the melts were homogeneously emulsified by a homomixer. The emulsion was cooled to obtain the emolient cream. This emolient cream produced a fully satisfactory sensation of use.

Stearic acid 2.0%

Stearyl alcohol 3.0%

Compound of Example 11 10.0%

Reduced lanolin 2.0%

Squalane 5.0%

Polyoxyethylene (25) cetyl ether 3.0%

Glycerin monostearate 2.0%

Perfume 0.3%

Antiseptic-antioxidant Suitable amount

Propylene glycol 5.0%

Purified water 67.7%

(Details as detergent)

Examples 45 and 46

The compounds of Examples 4 and 5 were rated for the following items as a detergent. The results are shown in Table 3.

(Rating of performance)

1. Penetrating Power

This property was determined by driving a 20-ounce roller piece, 90 mm×10 mm, made of wool conforming to JIS K-3362-1955 made by Japan Wood Textile Co., Ltd. at 25° C. on a sample containing the active principle in a concentration of 0.1 wt. %.

2. Deterging Force

This property was tested under the following conditions by the use of a stirring type detergency testing device (Terg-o-tometer), based on JIS K-3362.

Polluted fabric: 5 cm×5 cm in area

Polluting substances (% by weight): 28.3 of oleic acid, 15.6 of triolein, 12.2 of cholesterol oleate, 2.5 of liquid paraffin, 2.5 of squalane, 1.6 of cholesterol, 7.0 of gelatin, 29.8 of red yellow clay, and 0.5 of carbon black.

Water used: City water

Temperature: 25° C.

Deterging time: 5 minutes of washing and 5 minutes of rinsing

Bath ratio: Three fabrics/1 plot (1 liter)

Concentration of active principle: 0.03 wt. %

(Method for rating deterging force)

Test fabrics before pollution, after pollution, and after detergency of polluting matter were each examined at three points per fabric by the use of a reflectometer and the deterging force of a sample (%) is calculated by the following formula using the averages of the numerals obtained of the test fabrics.

Deterging force (%)=(Rw−Rs)/(Ro−Rs)(×100) wherein Rw represents the reflectance of a fabric after the detergence, Rs the reflectance of a polluted fabric, and Ro the reflectance of the fabric before pollution.

3. Foaming and Sensation of Foam

A sample, prepared in the form of an aqueous 30% solution, was actually used by a panel of five members and rated on the three-point scale, wherein ○ stands for excellent, Δ for ordinary, and x for inferior.

TABLE 3

| Example | 45 | 46 |
|---|---|---|
| Compound (Example) | 4 | 5 |
| Number of carbon atoms of olefin | 12 | 12 |
| Addition alkylene glycol | EG | TEG |
| Number of addition moles of EO | 7.3 | |
| Number of addition moles of PO | | |
| Number of addition moles of EO | | |
| Derivative | EC | EC |
| Penetrating force (sec) | 7 | 6 |
| Deterging force (%) | 75 | 68 |
| Foaming | ○ | ○ |
| Sensation of foam | ○ | ○ |

EG: Ethylene glycol
TEG: Triethylene glycol
EC: Ether carboxylic acid

Example 47

The compound of Example 3 was tested for penetrating force, deterging force, and foaming property. The penetrating force and the deterging force were tested in the same manner as in Examples 45–56 and the foaming property was tested by subjecting an aqueous 0.1% solution of a sample by the Ross-Miles method (in accordance with JIS K-3362 with modifications) under the condition of 25° C. The results are shown in Table 4. It is noted from the results that the compound not merely excelled in penetrating force and deterging force but also functioned as an excellent scouring agent for metals and fibers on account of low foaming property and foam rupturing property.

TABLE 4

| Example | 47 |
|---|---|
| Compound (Example) | 3 |
| Number of carbon atoms of olefin | 12 |
| Addition alkylene glycol | EG |
| Number of addition moles of EO | 7.3 |
| Number of addition moles of PO | |
| Number of addition moles of EO | |
| Derivative | Me |
| Penetrating force (sec) | 7 |
| Deterging force (%) | 69 |
| Foaming property (mm) | |

TABLE 4-continued

| Example | 47 |
|---|---|
| Foaming property (Immediately after foaming) | 100 |
| Foaming property (Three minutes after the foaming) | 10 |

EO: Ethylene glycol
Me: Methyl ether

Industrial Applicability

Since the (poly)alkylene glycol higher alkyl ether derivative composition contains virtually no alcohol component in the monoether as the raw material, it possesses such characteristic features as containing no oil-soluble component of low molecular weight, emitting odor sparingly, exhibiting a low stimulating property, having no foaming property, abounding in penetrating force, allowing thorough separation of the foam from a deterged article, and enjoying such low viscosity as to allow great ease of handling.

The (poly)alkylene glycol higher alkyl ether derivative composition of this invention, therefore, can be advantageously utilized as deterging agent, lubricating agent, dermatological medicine for external use, solvent, plasticizer, and polymerizing monomer.

What is claimed is:

1. A (poly)alkylene glycol higher alkyl ether derivative composition characterized by comprising 30–90 mol. % of (B1) (poly)alkylene glycol higher alkyl ether derivative and 70–10 mol. % of (B2) (poly)alkylene glycol higher alkyl ether derivative, respectively having a methyl group for $R^1$ and an alkyl group of not less than two carbon atoms for $R^1$ in the general formula (1) representing the derivatives:

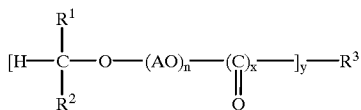

(1)

(wherein $R^1$ and $R^2$ represent alkyl groups whose total number of carbon atoms is in the range of 7–29, the number of carbon atoms of $R^2$ is larger than the number of carbon atoms of $R^1$, A represents a lower alkylene group, n represents a real number in the range of 1–300 on average, x represents 0 or 1, y represents a real number in the range of 1–10 on average, and $R^3$ represents an optionally substituted organic residue of 1–60 carbon atoms [excluding the carbon atoms of the substituent]).

2. A (poly)alkylene glycol higher alkyl ether derivative composition according to claim 1, wherein the composition has an alkylene group of 2–4 carbon atoms, 0 for x, 1 for y, and an alkyl group of 1–50 carbon atoms, a cycloalkyl group, an alkenyl group, or an aryl group for $R^3$, in the general formula (1).

3. A (poly)alkylene glycol higher alkyl ether derivative composition according to claim 1, wherein the composition has an alkylene group of 2–4 carbon atoms for A, 1 for x, a real number in the range of 1–4 on average for y, and $R^5[COOM]_z$ for $R^3$, in the general formula (1), providing $R^5$ represents a hydrocarbon residue of 1–60 carbon atoms, M represents an hydrogen atom, an alkali metal atom, an alkaline earth metal atom, an ammonium group, or an alkanol ammonium group, z represents a real number in the range of 0–3, and y+z represents a real number in the range of 1–4.

4. A (poly)alkylene glycol higher alkyl ether derivative composition according to claim 1, wherein the composition has an alkylene group of 2–4 carbon atoms for A, 1 for x, 1 for y, and a residue remaining after the exclusion of the carboxyl group from a monohydroxy monocarboxylic acid of 10–24 carbon atoms or the residue remaining after the exclusion of the carboxyl group from a (poly)ester derived from the condensation of a monohdroxy monocarboxylic acid of 10–24 carbon atoms for $R^3$ in the general formula (1).

* * * * *